(12) United States Patent
Anderson et al.

(10) Patent No.: US 10,028,435 B2
(45) Date of Patent: Jul. 24, 2018

(54) SENSOR CALIBRATION USING FIELD INFORMATION

(71) Applicant: Deere & Company, Moline, IL (US)

(72) Inventors: Noel W. Anderson, Fargo, ND (US); Aaron M. Senneff, Ankeny, IA (US); Jill M. Stanford, Cumming, IA (US); Henry H. Roark, III, Champaign, IL (US)

(73) Assignee: Deere & Company, Moline, IL (US)

( * ) Notice: Subject to any disclaimer, the term of this patent is extended or adjusted under 35 U.S.C. 154(b) by 326 days.

(21) Appl. No.: 15/061,108

(22) Filed: Mar. 4, 2016

(65) Prior Publication Data

US 2017/0251600 A1 Sep. 7, 2017

(51) Int. Cl.
*G01D 18/00* (2006.01)
*A01D 41/127* (2006.01)
*G01N 33/00* (2006.01)

(52) U.S. Cl.
CPC ..... *A01D 41/1271* (2013.01); *A01D 41/1273* (2013.01); *A01D 41/1276* (2013.01); *G01D 18/00* (2013.01); *G01N 33/0098* (2013.01)

(58) Field of Classification Search
CPC ............. A01D 41/127; A01D 41/1272; A01D 34/006; G01N 33/0098; G01N 21/00; G01N 2021/1793
See application file for complete search history.

(56) References Cited

U.S. PATENT DOCUMENTS

| 8,731,836 | B2 | 5/2014 | Lindores et al. |
| 9,058,633 | B2 * | 6/2015 | Lindores ................ G06Q 10/06 |
| 9,144,195 | B2 * | 9/2015 | Koch ................. A01D 41/1272 |
| 9,310,329 | B2 * | 4/2016 | Acheson .............. G01N 27/223 |
| 2014/0107957 | A1 * | 4/2014 | Lindores ............. A01B 79/005 |
| | | | 702/85 |
| 2014/0230391 | A1 | 8/2014 | Hendrickson et al. |
| 2014/0331631 | A1 | 11/2014 | Sauder et al. |

* cited by examiner

*Primary Examiner* — Jaehwan Oh
(74) *Attorney, Agent, or Firm* — Joseph R. Kelly; Kelly, Holt & Christenson PLLC

(57) ABSTRACT

A topographical indication for a field is detected by an aerial sensor and, based on the topographical indication, an area of consistent elevation is calculated. An estimated yield indication for a field is also detected, and an area of consistent estimated yield is calculated. With a controller, a calibration candidate zone is generated, wherein the calibration candidate zone comprises an area of the field with a consistent topography and a consistent estimated yield along a width and a length of the area.

20 Claims, 13 Drawing Sheets

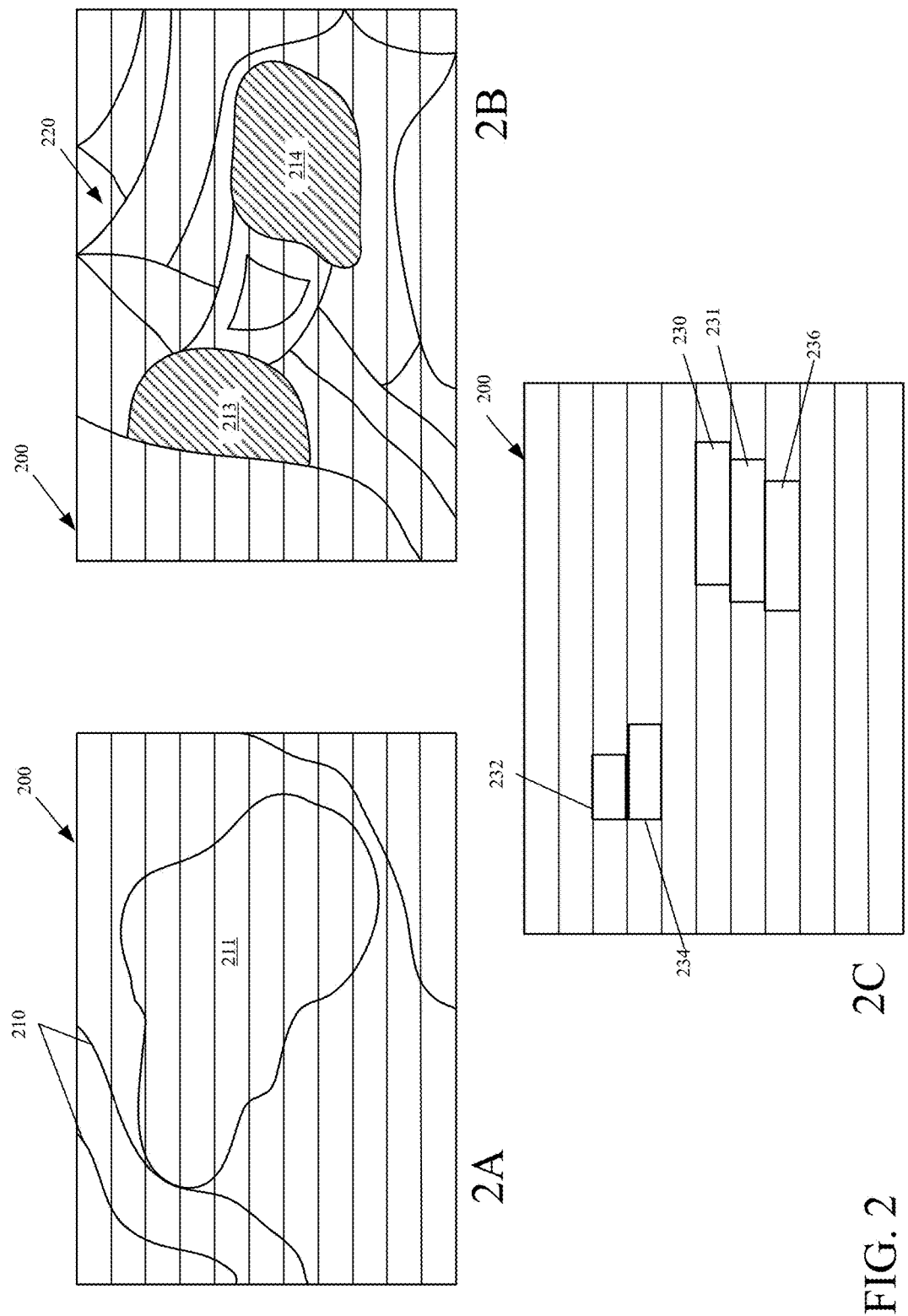

SENSOR CALIBRATION USING FIELD INFORMATION

FIELD OF THE DESCRIPTION

The present description relates to crop harvesting. More specifically, the present description relates to sensor calibration of crop harvesting equipment.

BACKGROUND

Harvesters are one type of field device available to farmers. A harvester is primarily responsible for harvesting crop from a field at the end of a growing season. Harvesters have one or more yield sensors responsible for detecting and reporting sectional and aggregate yield information as the harvester progresses through the field.

The discussion above is merely provided for general background information and is not intended to be used as an aid in determining the scope of the claimed subject matter.

SUMMARY

An estimated yield indication for portions of a field is detected. An area of consistent estimated yield is identified based on the estimated yield indication. A candidate calibration zone is identified as an area of the field with a consistent estimated yield.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

FIG. 2 (which includes FIGS. 2A-2C) shows different example views of a field growing crops.

DETAILED DESCRIPTION

Figure 1:
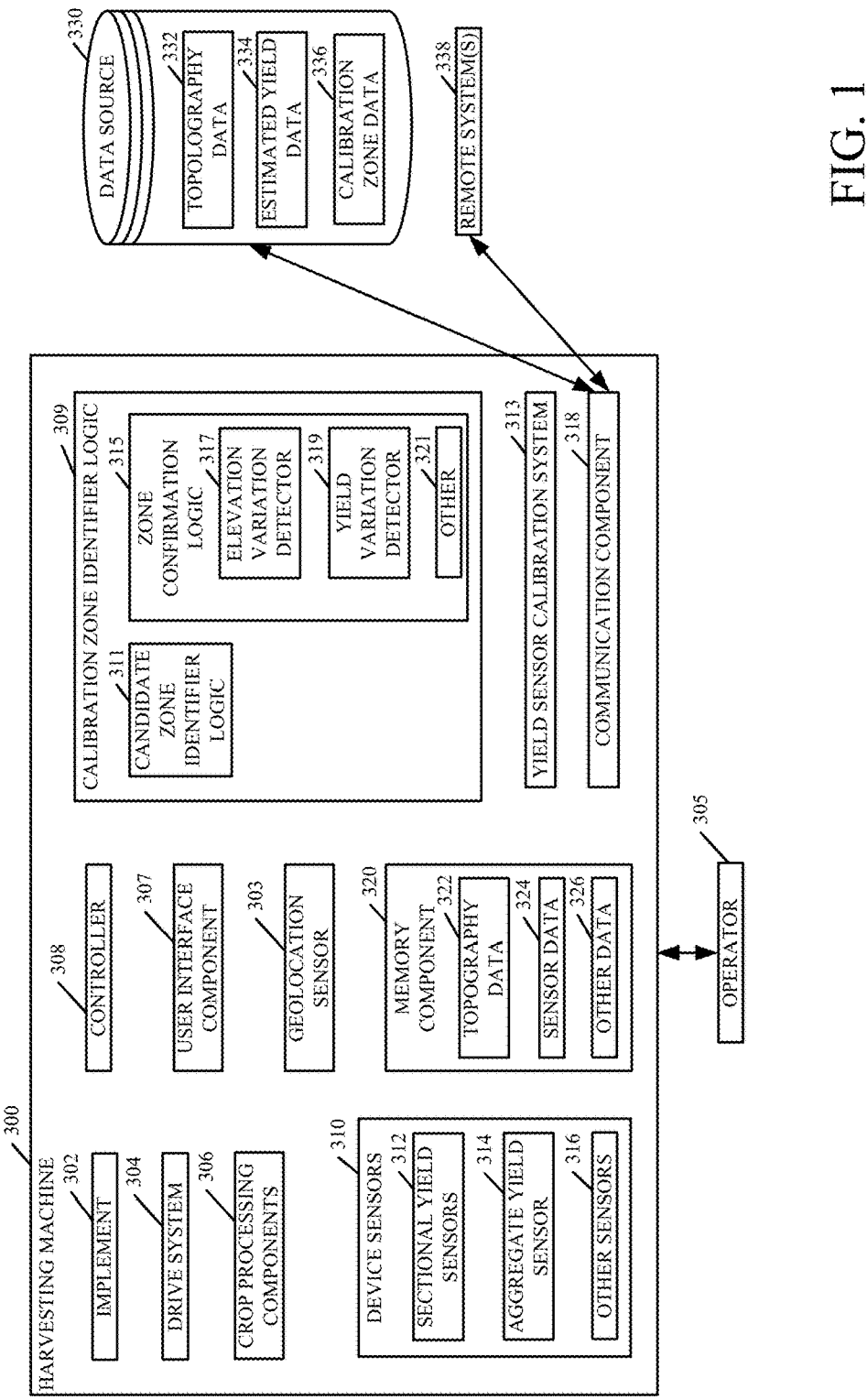
FIG. 1 is a simplified block diagram of one example of a harvesting machine.

FIG. 1 is a simplified block diagram of one example of portions of a harvesting machine (or machine) 300. FIG. 1 shows that harvesting machine 300 has an implement 302, for example a header or other harvesting mechanism. Harvesting machine 300, in one example, also has a propulsion system (or drive system) 304 that allows for at least some manual and/or automated control of harvesting machine 300. In one example, harvesting machine 300 also has one or more crop processing components (such as those discussed below with respect to FIGS. 1A and 1B) that are collectively shown in FIG. 3 by components 306. Such components can be configured to receive harvested crop, for example grain, process the received grain, and deliver the processed grain to a clean grain elevator which transfers it to a clean grain tank. Machine 300 can also have a user interface component that can include user interface mechanisms that can be used to surface information to a user (or operator) 305 and that can be manipulated by operator 305 to control machine 300.

Harvesting machine 300 can include geolocation sensor 303. Sensor 303 illustratively provides a signal indicative of the location of machine 300. Geolocation may be provided in global, regional or local coordinates. In some examples, sensor 303 is a global navigation satellite system (GNSS) receiver which provides geolocation as latitude and longitude coordinates. Other sensors can be used as well.

This information can be used in conjunction with, or appended to, any other sensor data to indicate where machine 300 was when the data was sensed. It can be used for navigation or in a wide variety of other ways as well.

In one example, harvesting machine 300 also has one or more device sensors 310. Sensors 310 can include one or more sectional yield sensors 312, aggregate yield sensors 314, or other sensors 316. Device sensors 310 can be located on any of crop processing components 306. Harvesting machine 300, in one example, also has a communication component 318 configured to communicate with one or more external data sources 330, or to other remote systems 338.

Sectional yield sensors 312, in one example, correspond to individual portions of a total harvest head width. For instance, they can be positioned to sense or measure plant or crop attributes corresponding to plants or crops engaged by different sections of the header as harvesting machine 300 moves through the field. These sensed attributes can be used to generate an estimate of yield corresponding to the different sections of the header. Aggregate yield sensors 314, in one example, sense aggregate yield (as discussed below) and can include such sensors as impact sensors, volumetric sensors, weight sensors, other mass flow sensors, or any other suitable sensors.

Sectional yield sensors 312 and aggregate yield sensors 314 may need calibration. However, in order to calibrate sensors 312 and 314, a calibration zone within a field being harvested is identified as a zone that has a relatively constant yield.

In one example, external data source 330 can have one or more sensors communicating sensor signals to harvesting machine 300 indicative of sensed data that is used to identify calibration zones in a field where machine 300 is operating. For instance, external data source 330 can be an aerial vehicle or a tenestrial vehicle, with sensors mounted on it. In another example, external data source 330 comprises a network data store accessible over a network, such as a cloud-based data store or web site accessible over the Internet. Also, harvesting machine 300, in one example, has a memory component 320, configured to store topographical data 322, sensor data 324, or other agricultural data 326, such as predicted yield data. These can be used to identify calibration zones.

Harvesting machine 300 also illustratively has a controller (or processor) 308, and calibration zone identifier logic 309. Logic 309, itself, illustratively includes candidate zone identifier logic 311 and zone confirmation logic 315 (which can include elevation variation detector 317, yield variation detector 319, and can include other items 321). Logic 309 (either by itself or under control of controller 308) receives topographical data 332 and estimated yield data 334, for example from external data source 330. Candidate zone identifier logic 311 identifies one or more candidate calibration zones (discussed below). Each zone can be represented by calibration zone data 336 that gives its geographic location and estimated yield (e.g., estimated aggregate and sectional yield). In another example, calibration zone data 336 can be calculated externally and provided to harvesting machine 300 through communication component 318.

Zone confirmation logic 315 can be used to confirm that a given candidate calibration zone should be used for calibration. This is also described below.

Machine 300 can also have a yield sensor calibration system 313. System 313 illustratively calibrates sensors 312 and 314 when machine 300 is in a confirmed calibration zone. System 313 may also simply determine whether calibration is needed, based on sensor data collected from a calibration zone, and the actual calibration can be performed separately.

Figure 1A:
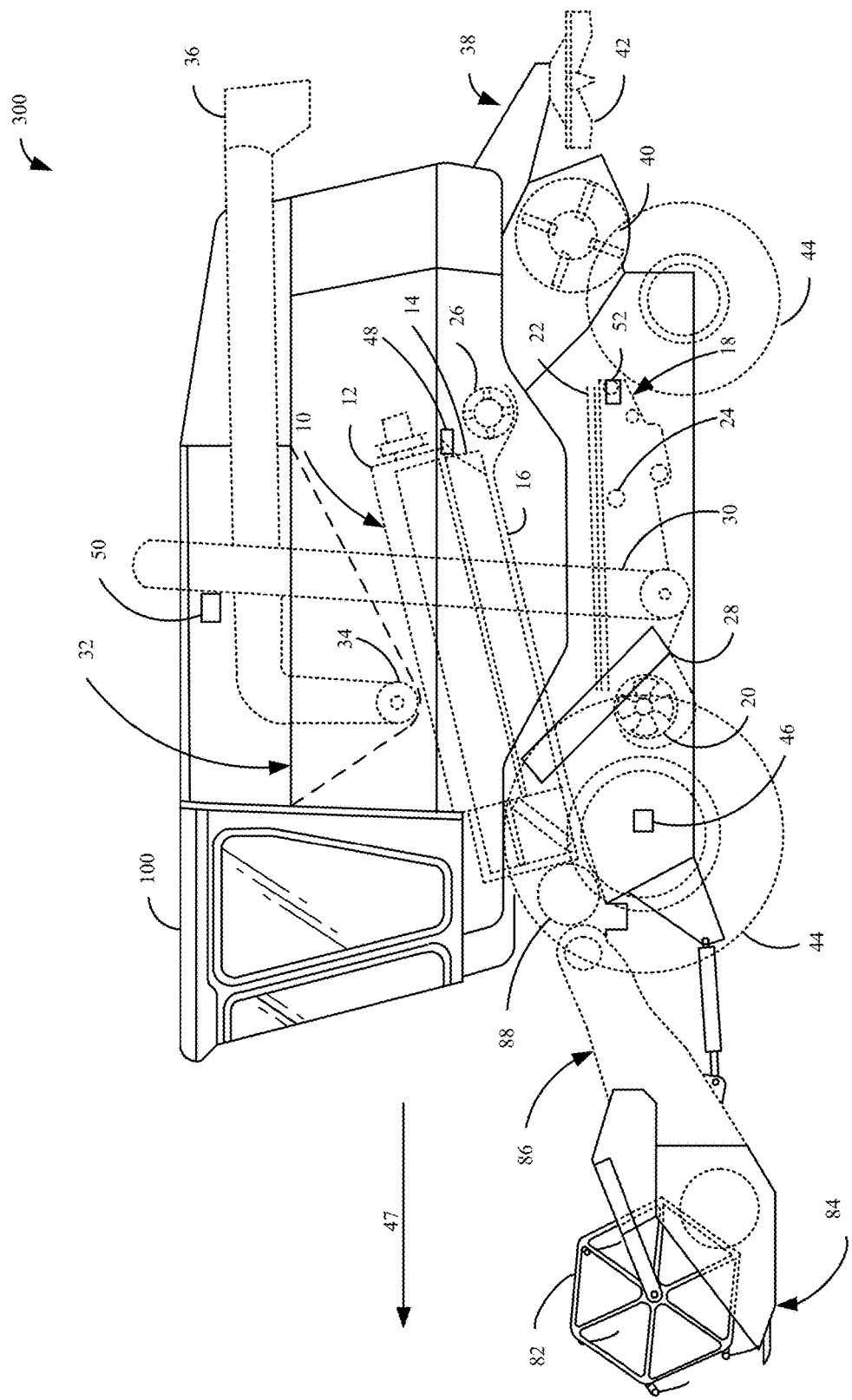
FIG. 1A is a pictorial, partial schematic view of one example in which the machine of FIG. 1 is a combine harvester.

FIG. 1A is a partial pictorial, partial schematic view of one example in which machine 300 is an agricultural machine such as a combine harvester. Machine 300 illustratively has an operator compartment 100, and a set of front end equipment. The front end equipment can, in one example, include header 82 and cutter 84. Machine 300 has, in one example, a feeder house 86, a feed accelerator 88, and a thresher 10. Thresher 10 can have a threshing rotor 12 and a set of concaves 14. Further, machine 300 has, in one example, a separator 16 with a separator rotor, and a cleaning subsystem (or cleaning shoe) 18 that, itself, can include a cleaning fan 20, chaffer 22 and sieve 24. Machine 300 can also include a discharge beater 26, tailings elevator 28, a clean grain elevator 30 (configured to move clean grain into clean grain tank 32) as well as unloading auger 34 and spout 36. It can also have a residue subsystem 38, with a chopper 40 and a spreader 42, and a propulsion subsystem with an engine that drives ground engaging wheels 44 or tracks, etc. Machine 300 can have more than one of any of the subsystems mentioned above, such as left and right cleaning shoes, separators, etc.

In operation, and by way of overview, machine 300 illustratively moves through a field in the direction indicated by arrow 47. As it moves, header 82 engages crop to be harvested and gathers it toward cutter 84. After it is cut, the crop moves, for example, through a conveyor in feeder house 86 toward feed accelerator 88, which accelerates crop into thresher 10. The crop is threshed, for example, by rotor 12 rotating the crop against concaves 14. The threshed crop is moved, for example, by a separator rotor in separator 16, where some of the residue is moved by discharge beater 26 toward the residue subsystem 38. The crop, in one example, is chopped by residue chopper 40 and spread on the field by spreader 42. In other implementations, for example, the residue is simply dropped in a windrow, instead of being chopped and spread.

The threshed and separated crop illustratively falls to cleaning shoe (or cleaning subsystem) 18. Chaffer 22, for example, separates some of the larger material from the clean crop, and sieve 24 separates some of the finer material from the clean crop. Clean crop (such as grain) then falls to an auger in clean grain elevator 30, which moves the clean grain upward and deposits it in clean grain tank 32. Residue is removed from cleaning shoe 18, for example, by air flow generated by cleaning fan 20. The residue can be moved rearwardly in machine 300 toward residue handling subsystem 38.

Tailings elevator 28 moves tailings, in one example, back to thresher 10 where they are re-threshed. In another example, the tailings pass to a separate re-threshing mechanism (also using a tailings elevator or other transport mechanism) for re-threshing.

Machine 300 has one or more sensors, including, for example: one or more ground speed sensors 46, separator loss sensors 48, clean grain cameras 50, and cleaning shoe loss sensors 52. Ground speed sensor 46, senses a travel speed of machine 300 over the ground. Sensor 46 can, for example, sense the rotational speed of the wheels, the drive shaft, the axel, or other components. Travel speed, in another example, is sensed by a positioning system, such as a global positioning system (GPS), a dead reckoning system, a Loran system, or a wide variety of other systems or sensors that provide an indication of travel speed.

Cleaning shoe loss sensors 52, in one example, provide an output signal indicative of the quantity of grain loss by either or both the right and left sides of cleaning shoe 18. In one example, sensors 52 are strike sensors configured to count grain strikes per unit of time (or per unit of distance traveled) to provide an indication of the cleaning shoe grain loss. The strike sensors for the right and left sides of the cleaning shoe can provide individual signals or a combined or aggregate signal. In one example, machine 300 only has a single sensor 52.

Separator loss sensors 48, in one example, provide a signal indicative of grain loss in the left and right separators. Sensors 48, associated with each of the left and right separators, provide separate grain loss signals.

It will also be appreciated that machine 300 can have other sensor/measurement mechanisms (in addition to the sensors already described). For example, machine 300 can have a machine state sensor configured to sense whether machine 300 is configured to chop the residue, drop a windrow, etc., cleaning shoe fan speed sensors proximate fan 20 that are configured to sense a fan speed, a material other than grain (MOG) moisture sensor configured to sense a moisture level of non-grain passing through machine 300 and a wide variety of other sensors. The sensors can also include a grain feed rate sensor that senses grain feed rate through clean grain elevator 30, or a mass flow rate through elevator 30, or other sensors.

It will be appreciated that there are a wide variety of different ways for measuring (or estimating) aggregate yield. One way is to sense the mass flow rate of harvested grain through clean grain elevator 30 and then to correlate it to a geographic position in the field from which that crop was harvested. One way of doing this is described below with respect to FIG. 1B. It will be understood that is only one example for measuring aggregate yield and many other ways can be used instead or in addition.

Figure 1B:
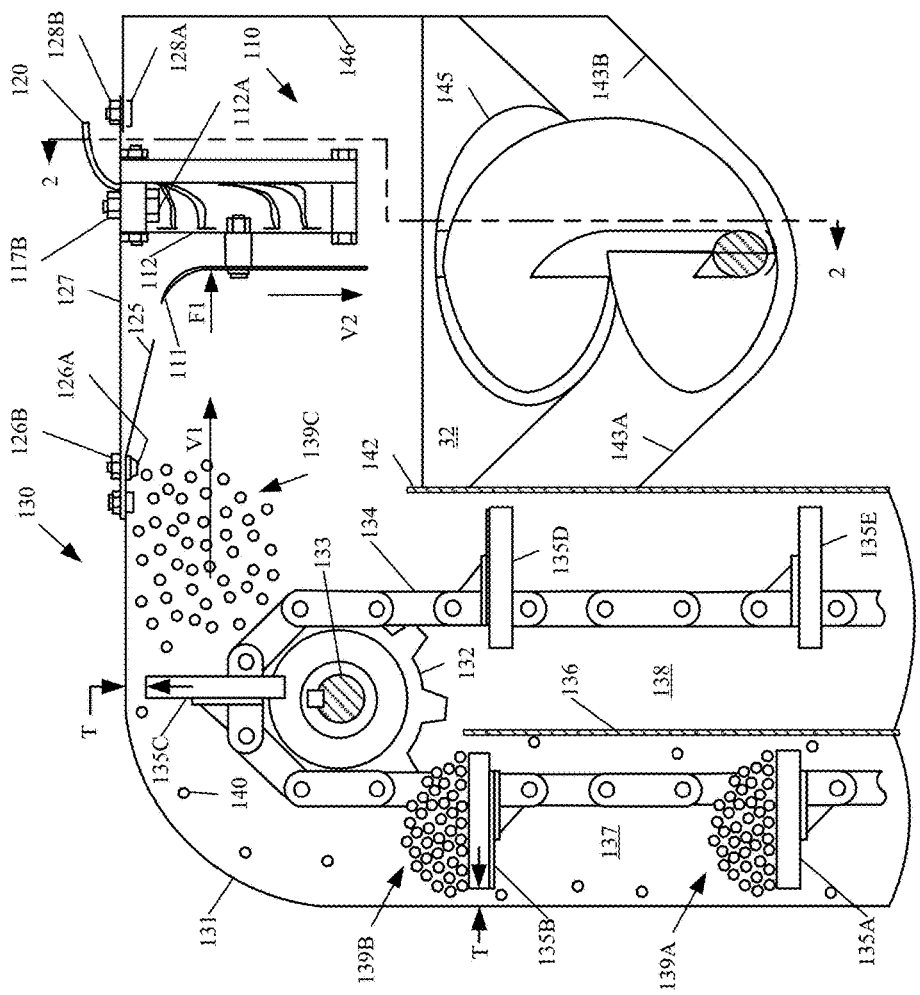
FIG. 1B shows one example of a cross section through a clean grain elevator of a combine.

FIG. 1B illustrates one example of a cross section through a clean grain elevator 30 of a combine. Clean grain elevator 30 of FIG. 1B may, for example, correspond to clean grain elevator 30, shown in FIG. 1A. A grain mass flow rate sensor 110 is positioned, in one example, at the outlet of clean grain elevator 30. Clean grain elevator 30 illustratively has an elevator housing 131 and a chain sprocket 132 which, for example, rotate with shaft 133 to drive a conveyor paddle chain 134. Conveyor paddle chain 134, in one example, wraps around sprocket 132 and attaches to paddles 135A-135E which lift grain from the inlet, to the outlet, of clean grain elevator 30. In one example, paddles 135A-135E attach to conveyor paddle chain 134 at regular intervals, such as at every fourth link, as shown in FIG. 1B. However, other attachment schemes can be used as well.

Clean grain elevator 30, in one example, has compartments 137 and 138, separated by divider plate 136. Sprocket 132, rotates clockwise (in the example shown in FIG. 1B), causing paddles 135A-135E to lift quantities of grain, for example, quantities 139A and 139B within compartment 137. When a chain link contacts sprocket 132, it rotates about shaft 133, which imparts a general horizontal motion to a quantity of grain, for example 139C, causing the grain to exit clean grain elevator 30 into a collection area 144. Clean grain tank 32, for example, has sloped lower surfaces 143A and 143B which cause grain to collect around an inlet end of unloading auger 34. After discharging grain into clean grain tank 32, the paddles travel downward within compartment 138 to the lower end of clean grain elevator 30 to collect new quantities of grain for delivery within compartment 137.

Grain mass flow rate sensor 110, in one example, has an impact plate 111 attached to a load beam 112. A quantity of grain, such as 139C, after leaving its paddle 135C, initially travels generally horizontally, at a velocity V1 toward impact plate 111. Upon striking impact plate 111, the horizontal motion of grain 139C is stopped, and the grain subsequently falls into clean grain tank 32 at a velocity V2, which is generally vertical. The change in the horizontal component of velocity of grain 139C from V1 to substantially zero corresponds to a change in the horizontal momentum of this quantity of grain which is proportional to both the mass of grain 139 and the velocity V1. A force F1, which is proportional to the change of momentum of grain 139, is created on impact plate 111 and is measured by load beam 112. Utilizing the measured F1, the mass flow of grain through elevator 30 (e.g., the yield) can be calculated. It is also possible, using geographic position coordinates, to correlate the yield measurements back to the geographical field locations over which the combine header was traveling when that grain was harvested.

It will also be appreciated that there are different ways of measuring (or estimating) sectional yield (which is the yield attributed to each row or section of the combine header). One way is to measure a plant attribute, at or near the interface where the header engages the plant, that is strongly related to yield, and then to assign a sectional yield based on that attribute and the correlated aggregate yield. Some such attributes may include the force of impact of harvested crop (e.g., ear of corn) on different sections of the header, the plant stalk size (e.g., diameter) encountered by each section, the energy used by each section in engaging the plant (e.g., hydraulic, electric, mechanical, etc.), the visual ear size engaged by each section (e.g., using image capture and analysis), among others.

One problem facing operators, for example using machine 300, is ensuring accurate yield measurements or estimates from sectional or aggregate yield sensors. Therefore, it may be desirable to calibrate such sensors. One potential method for calibrating sectional and aggregate yield sensors involves doing an offline calibration of the different sensors, or relying on a manufacturer completed calibration. However, as different portions of the combine experience different wear (for example based on use, etc.) it may be desirable to recalibrate some or all of the individual sensors.

In one example, in order to calibrate aggregate and sectional yield sensors, an in situ calibration measurement can be taken, for example, while the machine 300 is operating in the field. As is described in more detail below, a calibration zone is identified where a relatively accurate yield estimate can be made. The calibration zone is harvested and the estimated yield is compared to the measured aggregate and/or sectional yield in order to calculate sensor-specific error. Some example mechanisms and methods are described herein for calibrating sectional and aggregate yield sensors during a harvesting operation.

FIG. 2 includes FIGS. 2A-2C. FIGS. 2A-2C show different example views of a field growing crops. FIG. 2A illustrates one example of a topographical view of field 200, with topographical indicators 210 that provide sensed or measured elevation contours within field 200. Topographical indicators 210 can be used, in one example, to identify areas of consistent topography. In one example, calibration of sensors on machine 300 is performed in areas where the width of the header moves across a consistent elevation during the calibration period. FIG. 2A shows one example area 211 that has a consistent topography.

FIG. 2B illustrates one example view showing predicted or estimated yield throughout field 200, with different expected yield zones indicated by yield indicators 220. Estimated yields vary across field 200 for a variety of reasons, such as soil consistency, water availability, elevation, sunlight, etc. Predicted yields throughout field 200 can be estimated in a variety of ways, such as using aerial sensor information, land-based sensor information, or other sensor information. In one example, the calibration of sensors on machine 300 is performed in areas where the width of the header moves across an area that has consistent predicted yield during the calibration period. For instance, zones 213 and 214 in FIG. 2B have consistent estimated yield values (e.g., the yield values are consistent across zones 213 and 214, individually).

FIG. 2C illustrates one example a view of field 200 in which one or more candidate calibration zones 230, 231, 232, 234 and 236 (referred to as candidate calibration zones 230-236) are identified. Candidate calibration zones 230-236 can be calculated by combining the topographical information shown in FIG. 2A with the estimated yield data shown in FIG. 2B to detect suitable areas for an in-situ sensor calibration. In one example, candidate calibration zones 230-236 each have a consistent predicted yield and a consistent topography across their areas. Thus, they can be identified by intersecting area 211 in FIG. 2A (which is an area of consistent topography) with zones 213 and 214 in FIG. 2B (which are areas with consistent estimated yields.

Candidate calibration zones 230-236 can be calculated, at least in part, such that each zone is equal in width to, or greater in width than, the width of a combine header. Also, in one example, calibration candidate zones 230-236 are calculated, at least in part, based on a time period for machine 300 to reach steady state during a harvest operation. For example, the time period for harvested crop to travel from a header to an aggregate yield sensor on machine 300 can take time (such as 10 seconds). This is the time it takes for machine 300 to reach steady state, once it has entered a calibration zone. The steady state time period can be empirically measured from the time machine 300 first engages a crop to the time a yield sensor begins reporting yield measurements. The steady state time period, and time period over which the in-site calibration is performed, can be used to determine how big the calibration zone is to be. For instance, assume the steady state delay is 10 seconds, and assume that in one example, once the combine reaches steady state, the calibration is performed over the next 10 seconds. In such an example, candidate calibration zones 230-236 would need to cover at least 20 seconds of travel of machine 300. So, for example, if machine 300 is expected to travel at 3 feet per second, the candidate calibration zone would be at least 60 feet long, and, if the header is 8 rows wide, with a 24 inch row spacing, the candidate calibration zone, would be at least 16 feet wide.

Therefore, depending on available yield information and topographical information, candidate calibration zones 230-236 can be located in different areas within a field 200, for example as shown in FIG. 2C. In one example, calibration candidate zones 230-236 are ranked, based on the estimated degree of topographical and yield consistency. In one example, yield consistency may be defined as a percent variation of yield in each subregion (or portion of a candidate calibration zone) relative to the average yield for the whole region (of the candidate calibration zone). In another example, yield consistency may be the percentage of subregions within a certain range of the average for the whole region. In one example, topographical consistency may be defined as the maximum pitch or roll of a subregion of the candidate calibration zone within a region defining the candidate calibration zone. For instance, there may be multiple of each of: a first ranked candidate calibration zone 232, a second ranked candidate calibration zone 234, and a third ranked candidate calibration zone 236. In another example, candidate calibration zones 230-236 are ranked based on different estimated yields. For example, there may be a set of candidate calibration zones that are high yield zones 232, medium yield zones 234 or low yield zones 236. In another example, candidate calibration zones 230-236 are ranked or identified based on a travel speed of a combine through the zones. For example, there may be a set of high speed zones 232, medium speed zones 234, or low speed zones 236 so that machine 300 can be calibrated at high, medium and low travel speeds, respectively.

Topographical indicators 210 and yield indicators 220 can be obtained from a variety of sources. In one example, topographical and yield information is derived at least in part based on aerial sensor data, for example provided by a UAV, satellite, or other aerial-based sensor. The aerial sensor signals, in one example, comprise aerial imagery. In another example, the aerial sensor information is video information, or any other appropriate sensor information taken by an aerial sensor. The aerial sensor data can be any data that is indicative of topography and/or yield. For instance, it can be imagery showing crop health or size or other data indicative of estimated yield or estimated topography.

In one example, estimated yield data 334 may be derived from infrared or visual image sensors. The image data may be used to generate an index such as the Normalized Difference Vegetation Index (NDVI). The NDVI may be used to estimate relative or absolute yield with or without ground truthing. In another example, airborne LIDAR may be used to measure plant height above ground which is then converted to absolute or relative estimated yield data 334. In another example, estimated yield data 334 may be obtained from a crop model with or without ground truthing.

Once topographical and/or yield information is received, it is processed in order to identify topographical indicators 210 and yield indicators 220. In one example, a computing device within the machine 300 receives and processes topographical and/or yield information. In another example, an external computing device receives and processes topographical and/or yield information. In yet another example, the aerial sensor includes a computing device that processes the topographical and yield information and delivers topographical indicators 210, yield indicators 220, and zones 230-236 to the machine 300. Also, in one example, views of field 200 (for example those shown in FIGS. 2A, 2B, and 2C) are presented to a combine operator through a user interface, as described below, so the operator can initiate calibration when the combine enters a candidate calibration zone.

Figure 3:
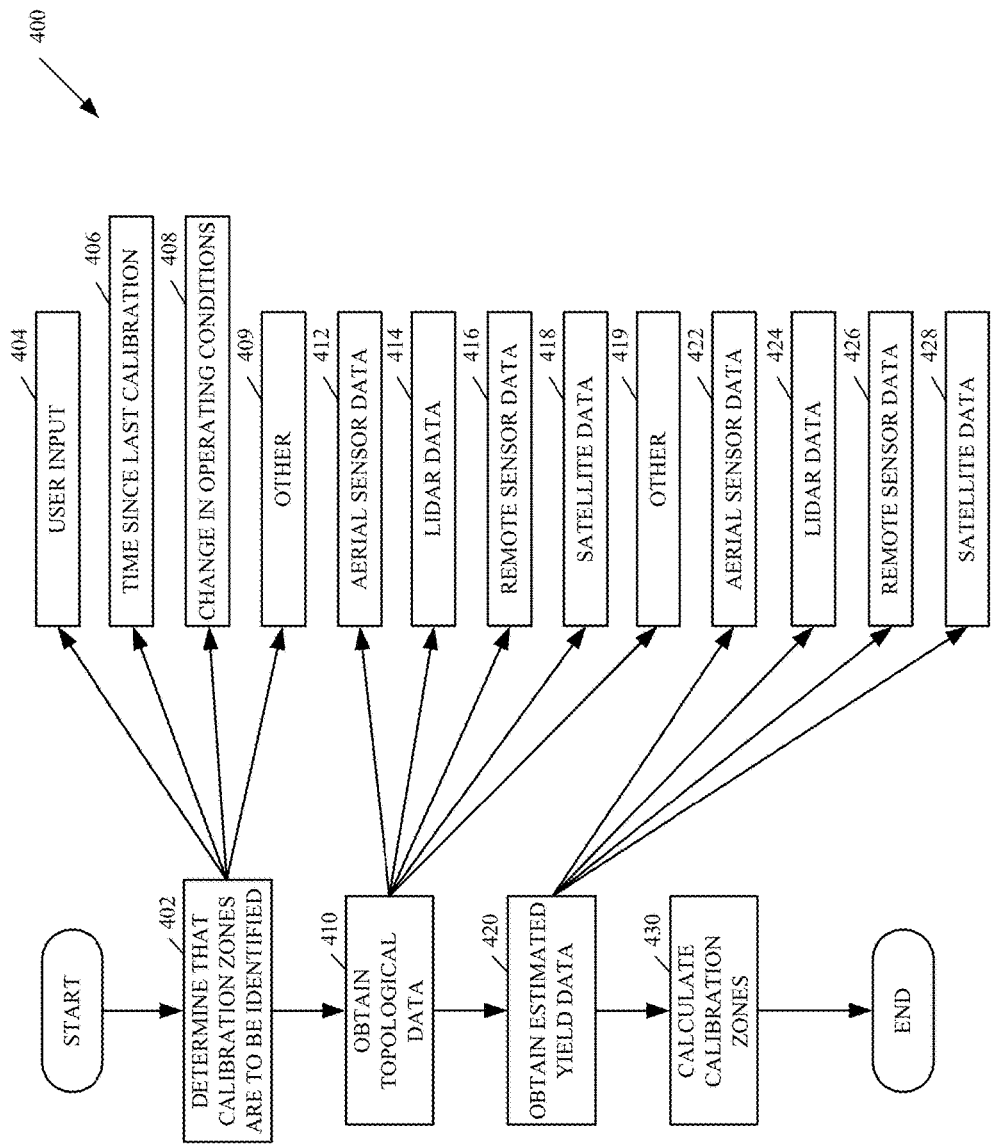
FIG. 3 shows a flow diagram of one example of calculating calibration candidate zones within a field.

FIG. 3 shows a flow diagram illustrating one example of the operation of calibration zone identifier logic 309 in identifying candidate calibration zones within a field. In one example, logic 309 identifies candidate calibration zones based on received topographical data and estimated yield data.

Logic 309 first determines that it is time to identify calibration zones. This is indicated by block 402. This can be determined by detecting a user input 404 requesting that calibration zones be identified. It can also be done automatically. For instance, logic 309 may identify calibration zones after a certain amount of time has passed since the sensors 310 were last calibrated. This is indicated by block 406. The zones may be identified if there is a detected change in operating conditions as indicated by block 408, or for other reasons, as indicated by block 409.

Calibration zone identifier logic 309 then receives topographical data for a field, for example topographical indicators 210 for field 200 (shown in FIG. 2). This is indicated by block 410. Topographical data, in one example, comprises elevation contours or other indicators throughout field 200. Topographical information can be obtained in a variety of ways. For example, it can be obtained from an aerial vehicle which provides aerial sensor data 412, from a Lidar system that provides it as Lidar data 414, from one or more other remote sensors that provide remote sensor information 416, from one or more satellites which provide, satellite data 418, or in other ways 419. Remote sensor data 416, for instance, can be obtained using a GPS receiver on a terrestrial vehicle. Also, in one example, machine 300 can receive topographical information and controller 308 can generate topographical indicators 210. In another example, topographical indicators 210 are generated externally relative to machine 300, and delivered through communication component 318. These are examples only.

Calibration zone identifier logic 309 then receives estimated yield data for the field. This is indicated by block 420. The estimated yield data can be generated from any one of a variety of sources. For example, it can be aerial sensor data 422, Lidar data 424, remote sensor data 426, or satellite data 428. Estimated yield indicators 220 (shown in FIG. 2B), in one example, are calculated by logic 309 within machine 300. In another example, estimated yield indicators 220 are generated by a processing unit external to machine 300.

Calibration zone identifier logic 309 then calculates one or more candidate calibration zones. This is indicated by block 430. Candidate calibration zones, for example zones 230-236 in FIG. 2C, can be calculated by correlating (e.g., overlaying) the estimated yield data and topographical data for the field, to detect areas with consistent topology and consistent estimated yield. Candidate calibration zones 230-236, are illustratively identified as areas that have at least a width that is as large as the width of the header, and long enough for the machine 300 to reach a steady state, given the travel speed of machine 300. They can be identified based on other criteria as well.

Figure 4:
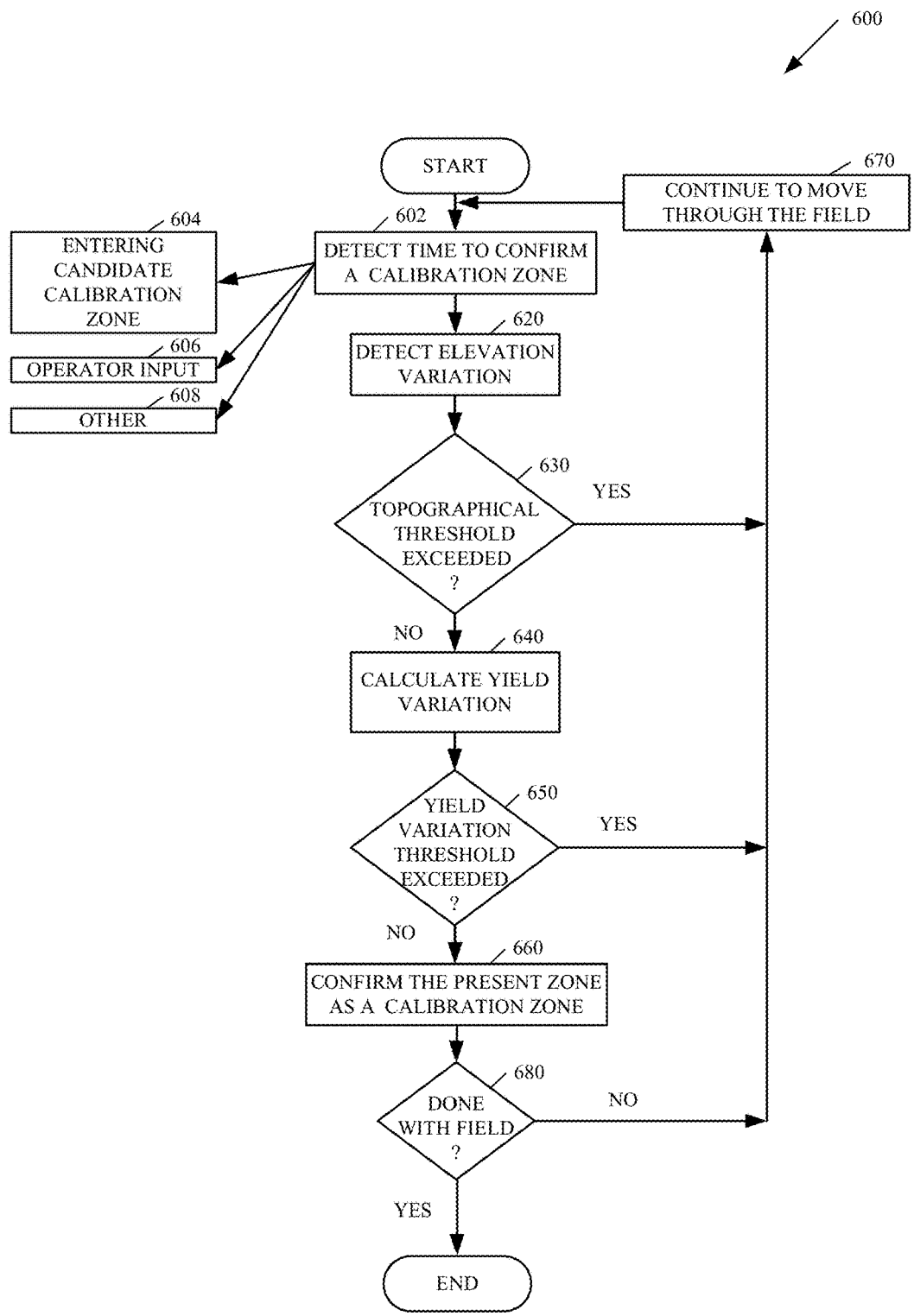
FIG. 4 shows a flow diagram illustrating one example of calibrating sensors within an agricultural machine.

FIG. 4 is a flow diagram illustrating one example of the operation of zone confirmation logic 315 in confirming a candidate calibration zone as a calibration zone that is to be used. FIGS. 2A-2C show candidate calibration zones 230-236. However, it may be that some of zones 230-236 have a predicted topography that does not correspond to actual topography conditions on the ground at harvest time. Additionally, estimated crop yield data may not reflect actual row-to-row variation within the field. Further, conditions may have changed since topographical indicators 210 or estimated yield indicators 220 were first obtained. Therefore, zone confirmation logic 315 can be used to confirm suitability of a given candidate calibration zone 230-236 for use in performing actual calibration.

Logic 315 first detects that it is time to confirm a candidate calibration zone. This is indicated by block 602. It can be done, for instance, by detecting positional information indicating that machine 300 is entering or approaching a candidate calibration zone. This is indicated by block 604. Positional information can be detected, in one example, by aerial sensors on an aerial vehicle, by position sensors on machine 300 (such as a GPS receiver) or in other ways. In another example, an operator provides an input that machine 300 is approaching or entering a candidate calibration zone. This is indicated by block 606. However, other detection mechanisms or techniques are also contemplated, as indicated by block 608.

Actual elevation variation within the identified candidate calibration zone (e.g., zone 230) is then detected. This is indicated by block 620. Elevation variation can be detected, for example by device sensors, such as an accelerometer, a GPS receiver that derives altitude, or other sensors. The elevation variation can also be detected through observation and by operator input, or using another appropriate mechanism for detecting elevation variation.

Zone confirmation logic 315 then compares the detected elevation variation with a topographical variation threshold, as indicated in block 630. In one example, if the topographical variation threshold is exceeded, the candidate calibration zone 230 is not used as a calibration zone for the machine 300, and machine 300 will continue to move through the field until another candidate calibration zone is detected, as indicated by block 670.

Assuming that the elevation variation is within the threshold level, it is then determined whether yield is relatively constant. Sectional and aggregate yield sensors 312, 314 generate sensor signals indicative of in-situ yield information, and yield variation detector 319 calculates a yield variation. In one example, the yield variation is not calculated until machine 300 reaches a steady state. Then, the sensed yield variation is compared against a yield variation threshold. The comparison, in one example, is conducted by yield variation detector 319. In another example, the sensed yield values can be sent to an external computing device, which performs the calculation. Determining whether the yield variation in the candidate calibration zone exceeds the threshold is indicated by block 650.

If the yield variation exceeds the variation threshold, the candidate calibration zone 230 will not be used for calibration, and machine 300 continues to move through field 200 until another candidate calibration zone is detected. This is indicated by block 670.

If the sensor signals indicative of topographical variation and yield variation for this candidate calibration zone 230 meet both the topographical variation threshold and the yield variation threshold, then zone 230 is confirmed as a calibration zone and can be used for calibration. In one example, machine 300 compares the yield sensor signals with expected yield values and determines which, if any, device sensors 310 should be replaced or calibrated. In another example, the sensor signals are output to an external processor, which conducts the analysis. Calibration is discussed in more detail below with respect to FIG. 5.

The different candidate calibration zones can be confirmed as described with respect to FIG. 4 until harvesting is complete. This confirmation helps to ensure that calibration is accurate. It will be appreciated that, in one example, a single calibration zone is used to calibrate one or more device sensors 310. In another example, a plurality of different calibration zones are used to calibrate device sensors 310. In yet another example, different calibration zones can be used to conduct calibration at different speeds, with different expected yield values, over different kinds of topography (such as on a side hill, or positive or negative gradient, etc.), among other things.

Figure 5:
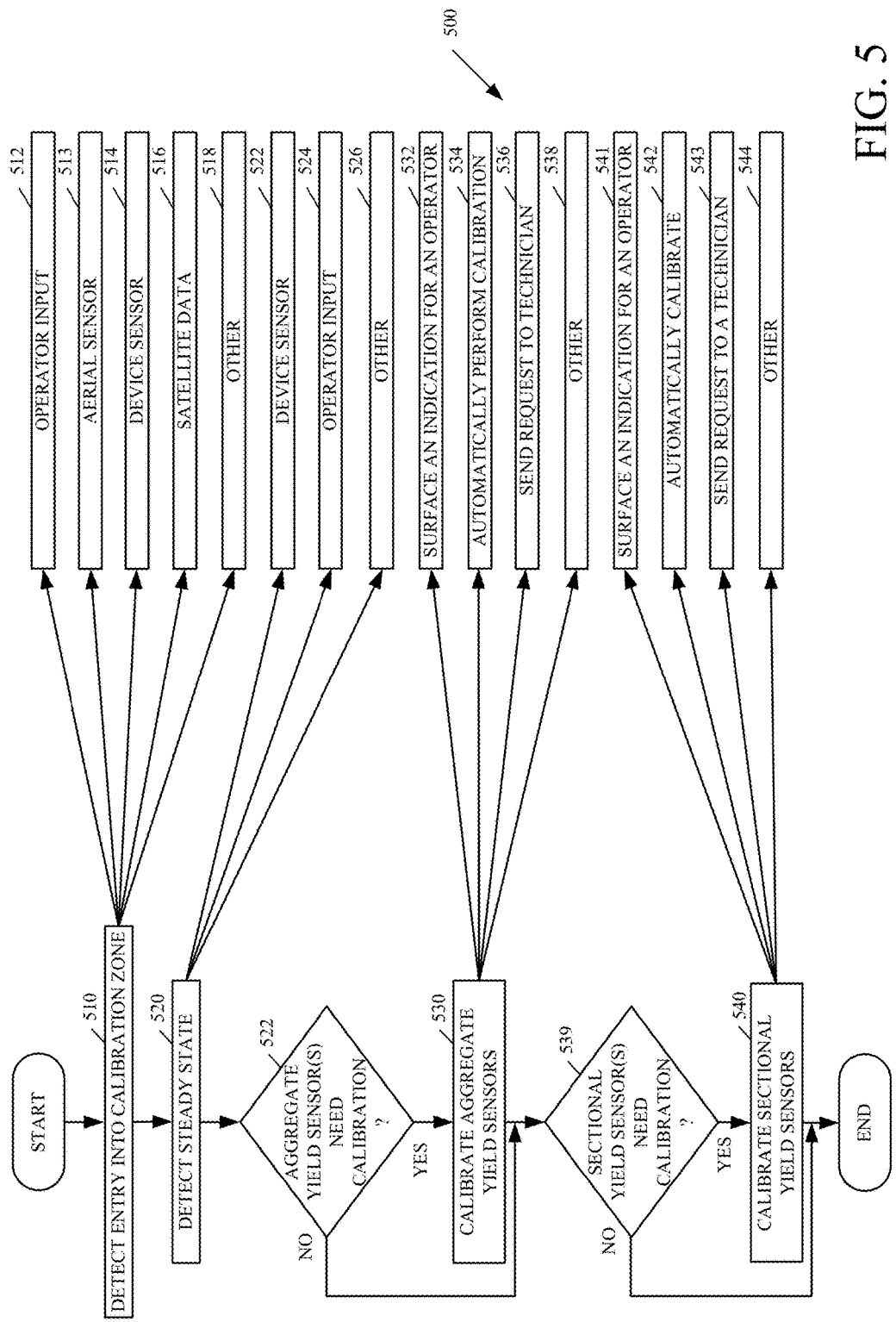
FIG. 5 shows a flow diagram illustrating one example of approving a calibration candidate zone as a calibration zone.

FIG. 5 shows a flow diagram illustrating one example of the operation of yield sensor calibration system (or calibration system) 313 in calibrating sensors within machine 300. In one example, calibration system 313 can simultaneously or sequentially calibrate a plurality of sensors on machine 300.

Calibration system 313 first detects that machine 300 is entering into a candidate calibration zone (e.g., zone 230). This is indicated by block 510. In one example, an operator visually determines that machine 300 is entering or approaching the candidate calibration zone 230 and provides an operator input to system 313. This is indicated in block 512. In another example, an aerial vehicle has an aerial sensor 513 that detects machine 300 entering or approaching the calibration zone. In another example, this is detected by another device sensor 514 (such as geolocation sensor 303, for example an internal GPS receiver or other location-based sensor within the machine 300). In yet another example, a satellite can provide satellite data 516, or another sensor can provide other sensor information 518, indicating that machine 300 is entering the calibration zone.

Calibration system 313 then detects that the machine 300 is harvesting at a steady state, within the calibration zone, as discussed above. This is indicated by block 520. Steady state, in one example, can be detected by one or more device sensors 522 or by operator input 524 (based on an operator observing that the machine 300 is at a steady state) or in other ways of detecting steady state 526.

Once steady state is reached in a calibration zone, one or more aggregate yield sensors can be calibrated. Calibration system 313 first determines whether the aggregate yield sensors are in need of calibration. This is indicated by block 522. To make this determination, calibration system 313 compares actual outputs of the aggregate yield sensors to estimated outputs of the aggregate yield sensors based on estimated yield data in the calibration zone. If the aggregate yield sensor signals show yield values within an acceptable margin of error relative to the estimated values, they are considered adequately calibrated. However, if the aggregate yield sensor signals are outside of an acceptable margin of error relative to expected signal levels, the sensors are considered in need of calibration (or replacement). This is indicated by block 530. In one example, an indication is sent to an operator, indicating that the aggregate yield sensor should be replaced, or calibrated, as indicated by block 532. In another example, the calibration is automatically performed by calibration system 313 as indicated by block 534. This can be done immediately, by adjusting weights assigned to the various sensor signals, or otherwise. It can also be done retroactively. For instance, the yield data generated prior to the calibration can be adjusted based on the calibration. Also, the calibration values (e.g., the weights assigned to the various sensor signals) can be stored and then applied later (e.g., they can be used to modify the yield values after the entire field is harvested, after a weight slip is received from an elevator, or at other times). In yet another example, a request for calibration or replacement is automatically sent to a technician or service person, as indicated by block 536. Calibration can be performed in other way as well, as indicated by block 538.

Then, it is determined whether one or more sectional yield sensors are to be calibrated. The determination can be made, for instance, by comparing actual sensor signal levels from the sectional yield sensors to estimated levels of sectional yield based on estimated yield data. In another example, since the yield may be estimated to be consistent across all sections of the header, then the sectional yield signals from each of the sectional yield sensors can be compared to one another to determine whether they are the same (within a threshold value) or whether they vary from one another (by more than the threshold value). If they do vary by more than the threshold value, then it can be determined that they are in need of calibration, since they should all be providing a similar yield signal.

If a sectional yield sensor signal value is outside of an acceptable margin of error relative to the estimated yield data, or relative to the other sectional yield sensors signals, the corresponding sensor may need calibration (or replacement). As with calibrating the aggregate yield sensor, the calibration of sectional yield sensors can include surfacing an indication that calibration is needed for the operator (as indicated by block 541), performing automatic calibration (as indicated by block 542), sending a request to a remote technician (as indicated in block 543), or in other ways (as indicated by block 544). In one example, a plurality of sectional yield sensors can be simultaneously calibrated in parallel. In another example, a single sectional yield sensor is calibrated at a time.

Figure 6:
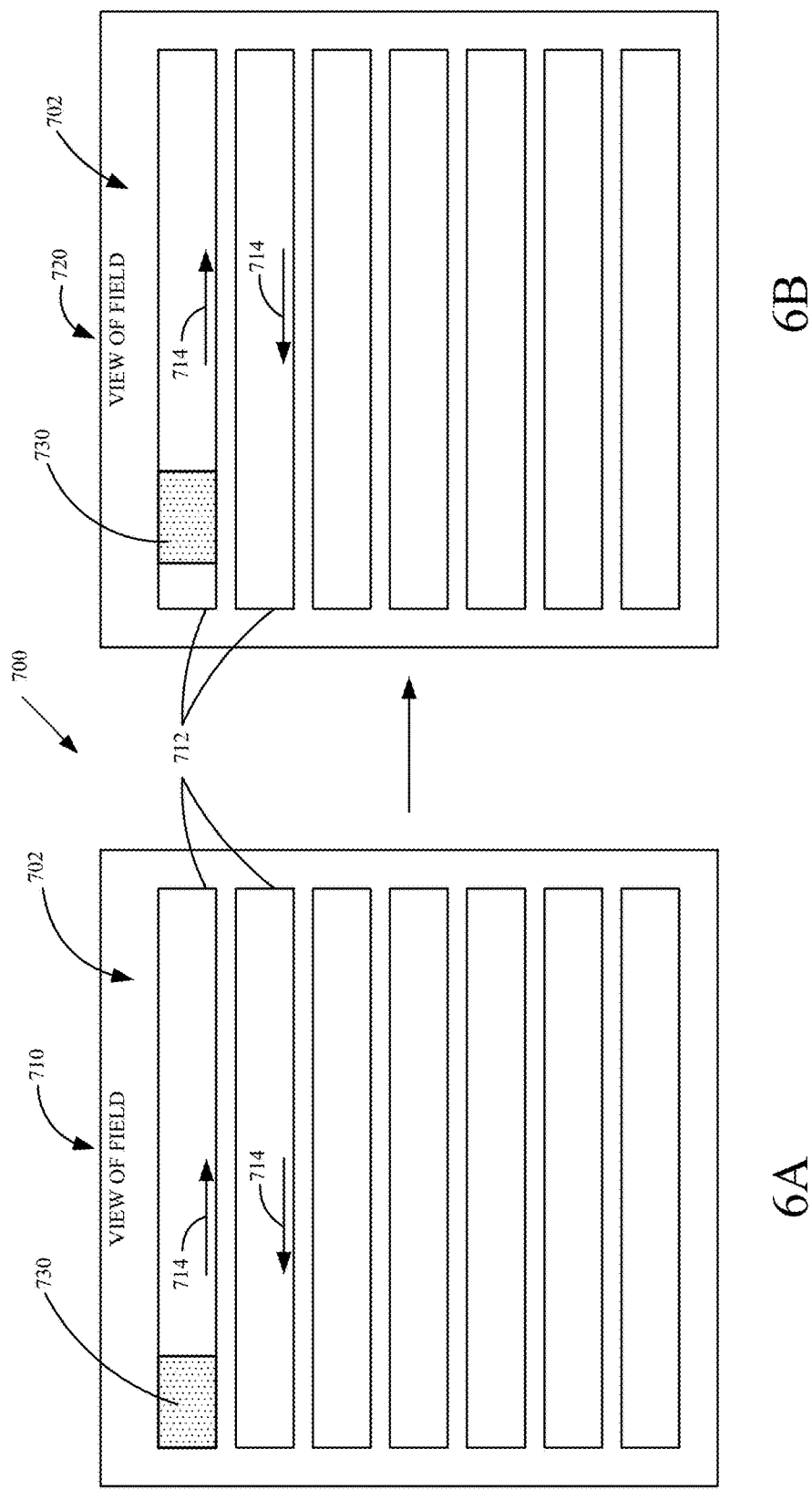
FIG. 6 (which includes FIGS. 6A and 6B) shows simplified example user interface views of a field during a calibration.

Thus far, the description has proceeded with respect to the calibration zones being identified ahead of time and then, possibly, confirmed during harvest. However, it is also contemplated that the calibration zones can be identified and confirmed, in near real time, during harvesting. FIGS. 6A and 6B illustrate this.

FIGS. 6A and 6B show a simplified example of user interface views of a field during a calibration. Views 710 and 720, in one example, are provided on a user interface for viewing by an operator within an operation compartment of machine 300. In another example, the user interface is provided on an external display to an individual other than an operator of machine 300. For the sake of illustration, but not by limitation, FIGS. 6A and 6B illustrate a single sliding window 730, that corresponds to a position of machine 300 within a field 702, and which is identified using current positional information received from a machine 300 within the field 702. However, in another example, where multiple agricultural machines are moving through field 702, a plurality of sliding windows 730 are presented that correspond to positional data received from each of the plurality of machines 300.

As shown in FIG. 6A, machine 300 moves through a series of passes (represented by display elements 712) in field 702. It is assumed that machine 300 is moving in the directions indicated by arrows 714. Each pass 712 is defined, at least in part, by the width of the header of machine 300. For each pass 712 through field 702, the sliding window 730 is initially placed at the beginning of the pass, corresponding to the position of machine 300 moving through field 702. As machine 300 moves across field 702, sliding window 730 correspondingly moves along the current pass 712 for machine 300. For instance, it can be seen that window 730 has moved from a first position in FIG. 6A to a second position, in the direction of movement 714, in FIG. 6B. As machine 300 moves through field 702, topography sensors and/or yield sensors are evaluated to determine topographical variation and yield variation, for example, as explained above. The topographical and yield variations are used in determining whether the geographical region represented by sliding window 730 can be used to perform yield sensor calibration. For example, a length (in the direction of machine travel) of sliding window 730 may increase (if conditions allow) for a longer calibration time, or decrease if variation in topography or yield are detected.

More specifically, as machine 300 moves through field 702, device sensors 310 detect topographical information and yield information. If the topographical variation exceeds a topographical variation threshold, then the sliding window 730 moves forward. In one example, sliding window 730 moves a preset distance down a current pass 712, for example, as shown in the transition from FIG. 6A to FIG. 6B. Sliding window 730 can move incrementally until a topographical variation is within the topographical variation threshold. Once an area is found where the topographical variation is within the threshold, sensed yield variation (sensed from aggregate and/or sectional yield sensors 312, 314) is compared to a yield variation threshold. If the yield variation is not within an acceptable range of the yield variation threshold, the sliding window 730 continues to move as discussed above.

Once an area corresponding to sliding window 730 is identified as having a relatively consistent topology and a relatively consistent yield, the area is marked as a calibration zone (e.g., zone 230), and calibration can be undertaken. However, in one example, topographical variation and yield variation, are continually measured as machine 300 moves through the calibration zone represented by sliding window 730. As long as those variations are acceptable, the calibration zone corresponding to sliding window 730 can be extended until a point at which topographical variation and/or yield variation exceed their corresponding thresholds. This allows, for example, for a longer calibration period to take place, providing more calibration data, and increasing calibration accuracy.

The present discussion of FIGS. 6A and 6B has proceeded with respect to determining first whether topographical variation is within a threshold, and then whether yield variation is within a threshold. It will be noted that the two could be reversed, or that only a single one (topographical variation or yield variation) can be considered or even different or additional criteria can be used. Also, thresholds for topographical variation and yield variation can take a wide variety of different forms. They can be expressed in terms of ranges, standard deviations, or any other suitable metric for determining an acceptable level. They can be determined empirically or otherwise.

Further, in one example, a calibration zone (e.g., zone 230) is defined by one or more parameters. Without limitation, some parameters used to define calibration zones can include: yield data, geographic position, topology information (such as harvester pitch, harvester roll, etc.), crop characteristics (such as estimated crop moisture, protein, oil, or starch content, crop health or vigor, plant population, etc.), soil characteristics (such as soil type, soil moisture, etc.) or other parameters such as crop variety, weed intensity, etc. Candidate calibration zones 230-236, in one example, can also be characterized by a corresponding crop flow rate. The flow rate is realized by a harvester, traveling at a given ground speed, causes a certain amount of grain to be sensed by yield sensors 312, 314 per unit time. In another example, calibration zones can be identified, based on estimated yield, as zones where the sensors can be calibrated at different yields (such as at a low flow rate, a medium flow rate, and/or a high flow rate). The corresponding calibration zones can then be assigned a corresponding harvester speed (such as a low harvester speed, a medium harvester speed, and/or a high harvester speed), for example. Thus, the yield sensors can be calibrated at different harvester speeds and different flow rates. In another example, calibration zones are designed to capture other operational characteristics besides different crop flow rates. For example, the calibration zones can be identified to calibrate the harvester on side hills and flat terrain, as well as on inclines or declines.

Also, the present discussion has proceeded with respect to examples in which the calibration zones are identified before, or simultaneously with, machine 300 moving over those zones. However, in at least one example, different calibration zones 230-236 are not identified and/or verified until a machine 300 has passed the zone, or even completed harvesting the corresponding field. For example, analysis of data from the one or more device sensors 310, which would indicate topographical or yield data that is outside of a given threshold, is not analyzed until after a harvest operation is complete. Therefore, in one example, machine 300 collects calibration data as it moves through all candidate calibration zones within a field, and determines which zones meet the required thresholds after a harvest is complete. It can then identify those zones as calibration zones and calibrate the yield sensors, retroactively, based on the data collected from those zones.

It will be noted that the above discussion has described a variety of different systems, components and/or logic. It will be appreciated that such systems, components and/or logic can be comprised of hardware items (such as processors and associated memory, or other processing components, some of which are described below) that perform the functions associated with those systems, components and/or logic. In addition, the systems, components and/or logic can be comprised of software that is loaded into a memory and is subsequently executed by a processor or server, or other computing component, as described below. It will be noted that the above discussion has described a variety of different systems, components and/or logic. The systems, components and/or logic can also be comprised of different combinations of hardware, software, firmware, etc., some examples of which are described below. These are only some examples of different structures that can be used to form the systems, components and/or logic described above. Other structures can be used as well. The present discussion has mentioned processors and servers. In one example, the processors and servers include computer processors with associated memory and timing circuitry, not separately shown. They are functional parts of the systems or devices to which they belong and are activated by, and facilitate the functionality of the other components or items in those systems.

Also, a number of user interface displays have been discussed. They can take a wide variety of different forms and can have a wide variety of different user actuatable input mechanisms disposed thereon. For instance, the user actuatable input mechanisms can be text boxes, check boxes, icons, links, drop-down menus, search boxes, etc. They can also be actuated in a wide variety of different ways. For instance, they can be actuated using a point and click device (such as a track ball or mouse). They can be actuated using hardware buttons, switches, a joystick or keyboard, thumb switches or thumb pads, etc. They can also be actuated using a virtual keyboard or other virtual actuators. In addition, where the screen on which they are displayed is a touch sensitive screen, they can be actuated using touch gestures. Also, where the device that displays them has speech recognition components, they can be actuated using speech commands.

A number of data stores have also been discussed. It will be noted they can each be broken into multiple data stores. All can be local to the systems accessing them, all can be remote, or some can be local while others are remote. All of these configurations are contemplated herein.

Also, the figures show a number of blocks with functionality ascribed to each block. It will be noted that fewer blocks can be used so the functionality is performed by fewer components. Also, more blocks can be used with the functionality distributed among more components.

Figure 7:
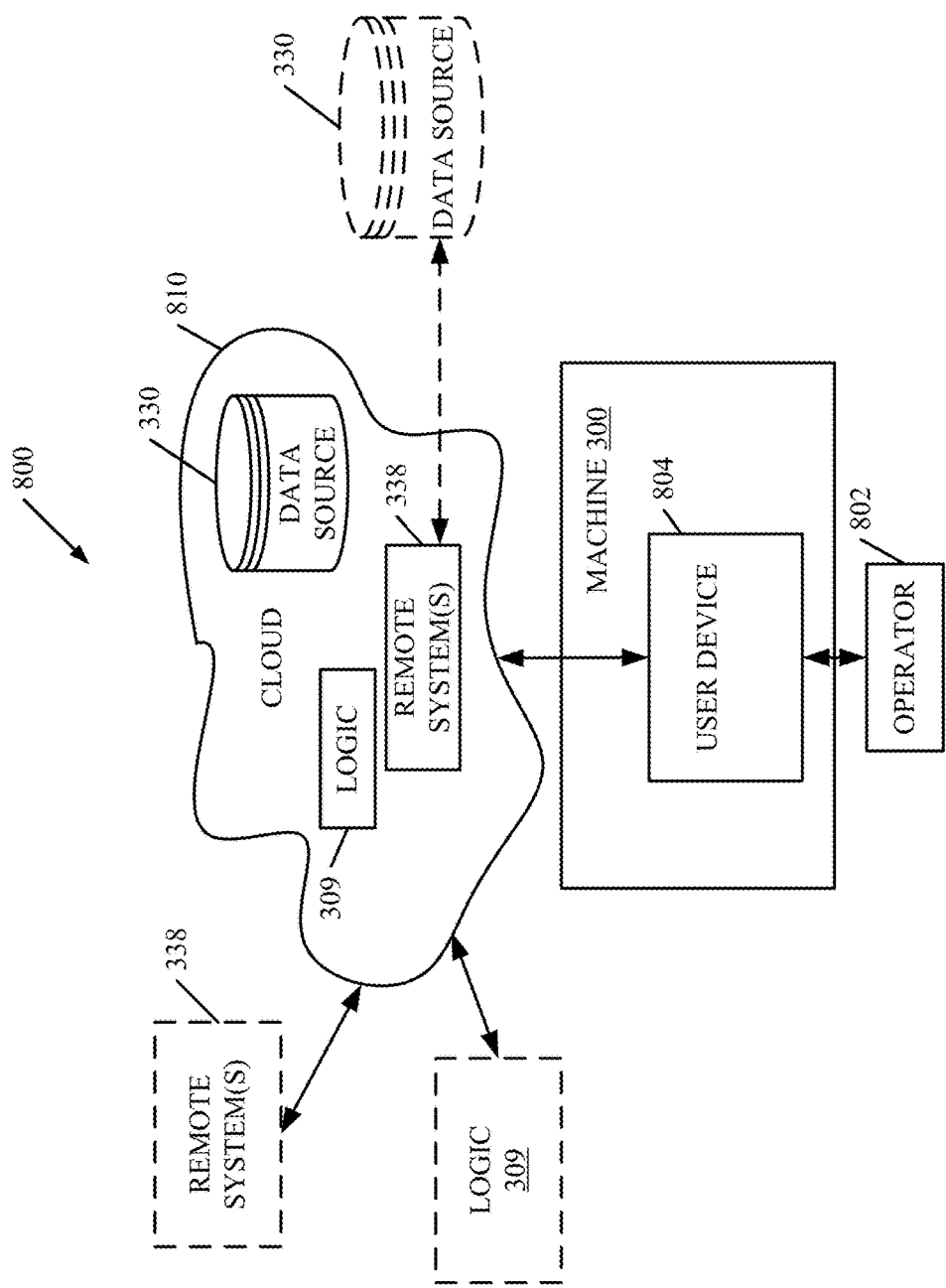
FIG. 7 is a block diagram of one example of a remote server architecture.

FIG. 7 is a block diagram of machine 300, shown in FIG. 1, except that it communicates with elements in a remote server architecture 800. In one example, remote server architecture 800 can provide computation, software, data access, and storage services that do not require end-user knowledge of the physical location or configuration of the system that delivers the services. In various examples, remote servers can deliver the services over a wide area network, such as the internet, using appropriate protocols. For instance, remote servers can deliver applications over a wide area network and they can be accessed through a web browser or any other computing component. Software or components shown in FIG. 1 as well as the corresponding data, can be stored on servers at a remote location. The computing resources in a remote server environment can be consolidated at a remote data center location or they can be dispersed. Remote server infrastructures can deliver services through shared data centers, even though they appear as a single point of access for the user. Thus, the components and functions described herein can be provided from a remote server at a remote location using a remote server architecture. Alternatively, they can be provided from a conventional server, or they can be installed on client devices directly, or in other ways.

In the example shown in FIG. 7, some items are similar to those shown in FIG. 1 and they are similarly numbered. FIG. 7 specifically shows that logic 309 and data source 330 can be located at a remote server location 802. Therefore, an operator 802 can use a user device 804 in machine 300 accesses those systems through remote server location 802.

FIG. 7 also depicts another example of a remote server architecture. FIG. 7 shows that it is also contemplated that some elements of FIG. 1 can be disposed at remote server location 802 while others are not. By way of example, data source 330 or remote systems 338 or logic 309 can be disposed at a location separate from location 802, and accessed through the remote server at location 802. Regardless of where they are located, they can be accessed directly by machine 300, through a network (either a wide area network or a local area network), they can be hosted at a remote site by a service, or they can be provided as a service, or accessed by a connection service that resides in a remote location. Also, the data can be stored in substantially any location and intermittently accessed by, or forwarded to, interested parties. For instance, physical carriers can be used instead of, or in addition to, electromagnetic wave carriers. In such an example, where cell coverage is poor or nonexistent, another mobile machine (such as a fuel truck) can have an automated information collection system. As the harvester comes close to the fuel truck for fueling, the system automatically collects the information from the harvester using any type of ad-hoc wireless connection. The collected information can then be forwarded to the main network as the fuel truck reaches a location where there is cellular coverage (or other wireless coverage). For instance, the fuel truck may enter a covered location when traveling to fuel other machines or when at a main fuel storage location. All of these architectures are contemplated herein. Further, the information can be stored on the harvester until the harvester enters a covered location. The harvester, itself, can then send the information to the main network.

It will also be noted that the elements of FIG. 1, or portions of them, can be disposed on a wide variety of different devices. Some of those devices include servers, desktop computers, laptop computers, tablet computers, or other mobile devices, such as palm top computers, cell phones, smart phones, multimedia players, personal digital assistants, etc.

Figure 8:
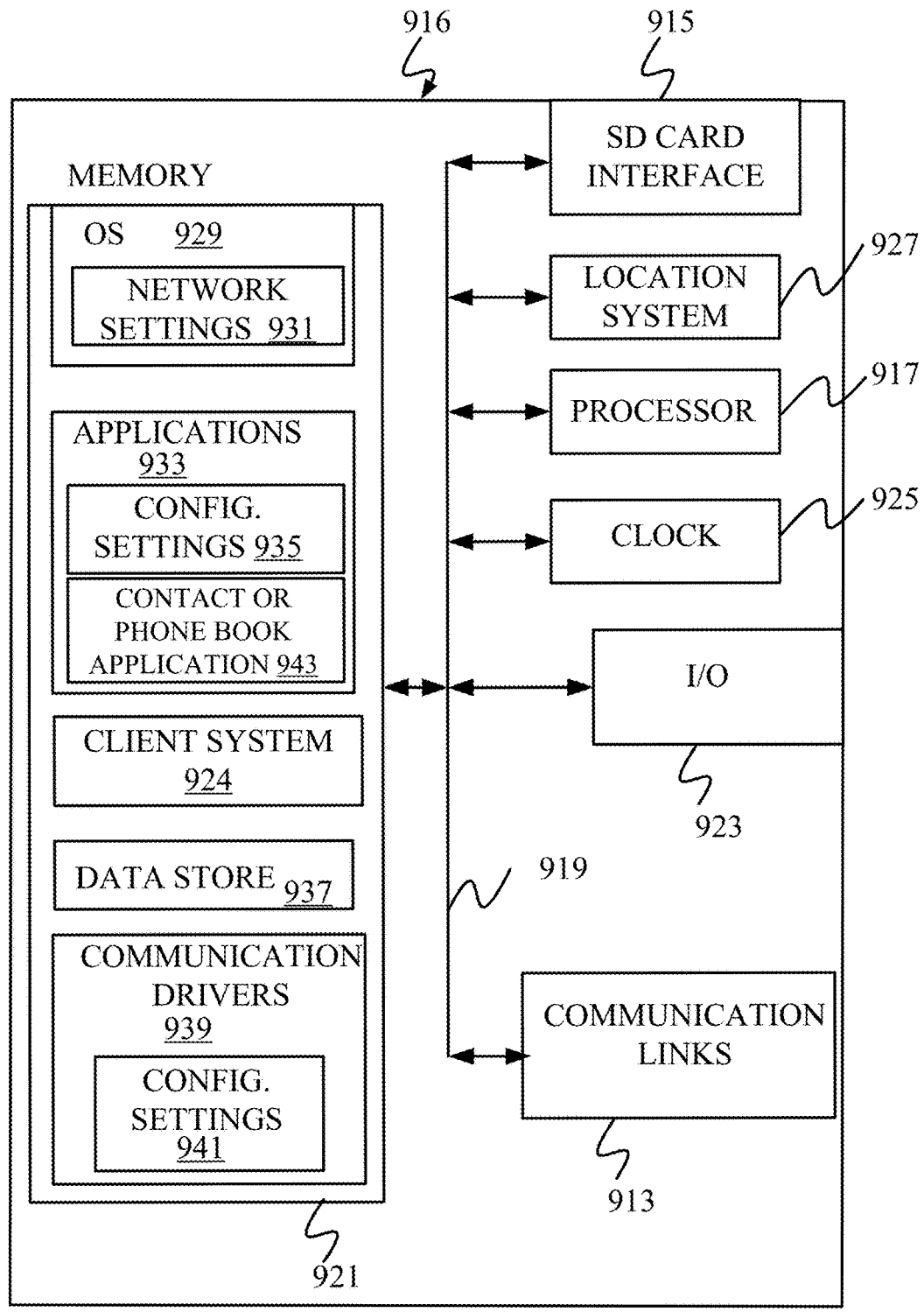
FIGS. 8-10 show examples of mobile devices.
Figure 9:
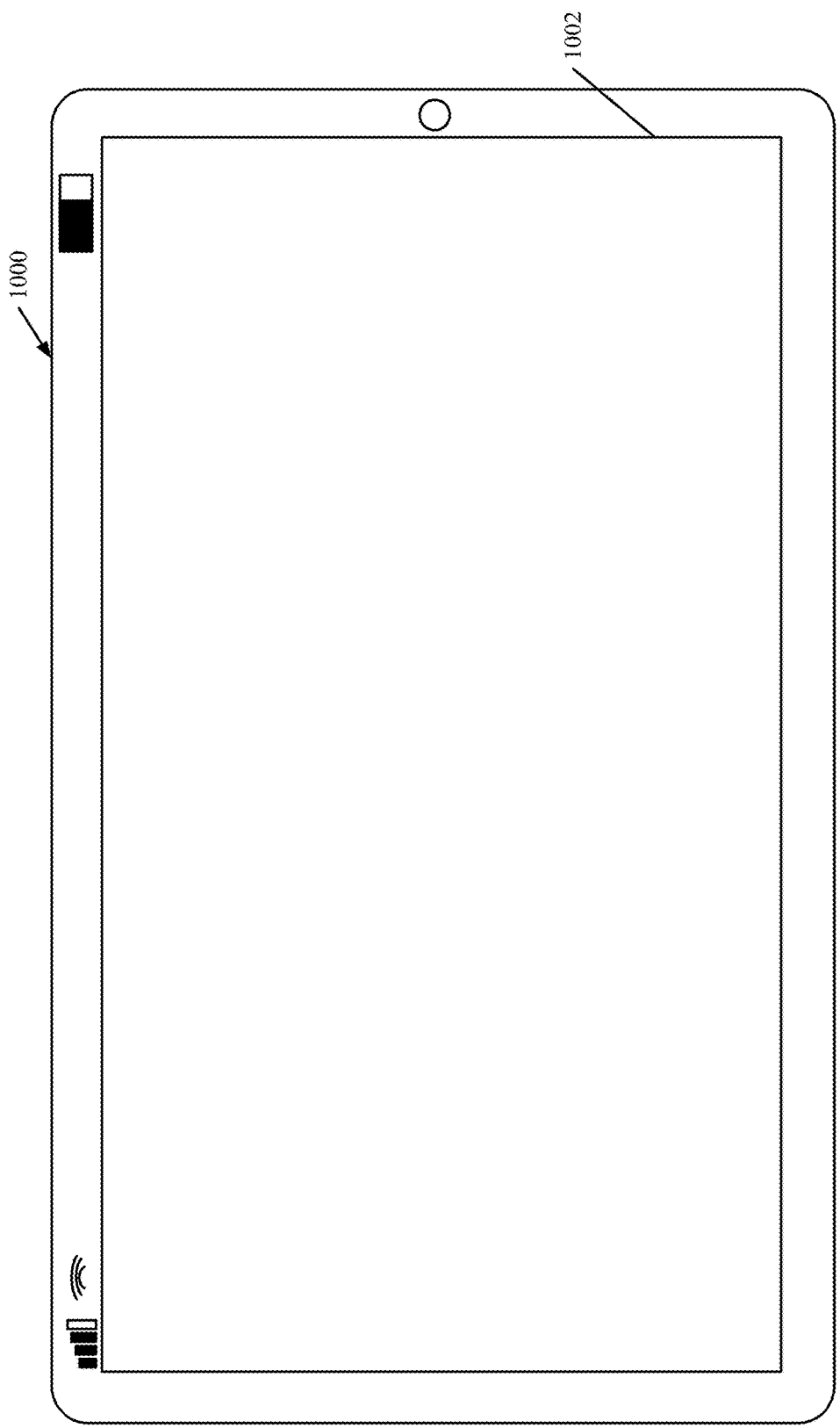
Figure 10:
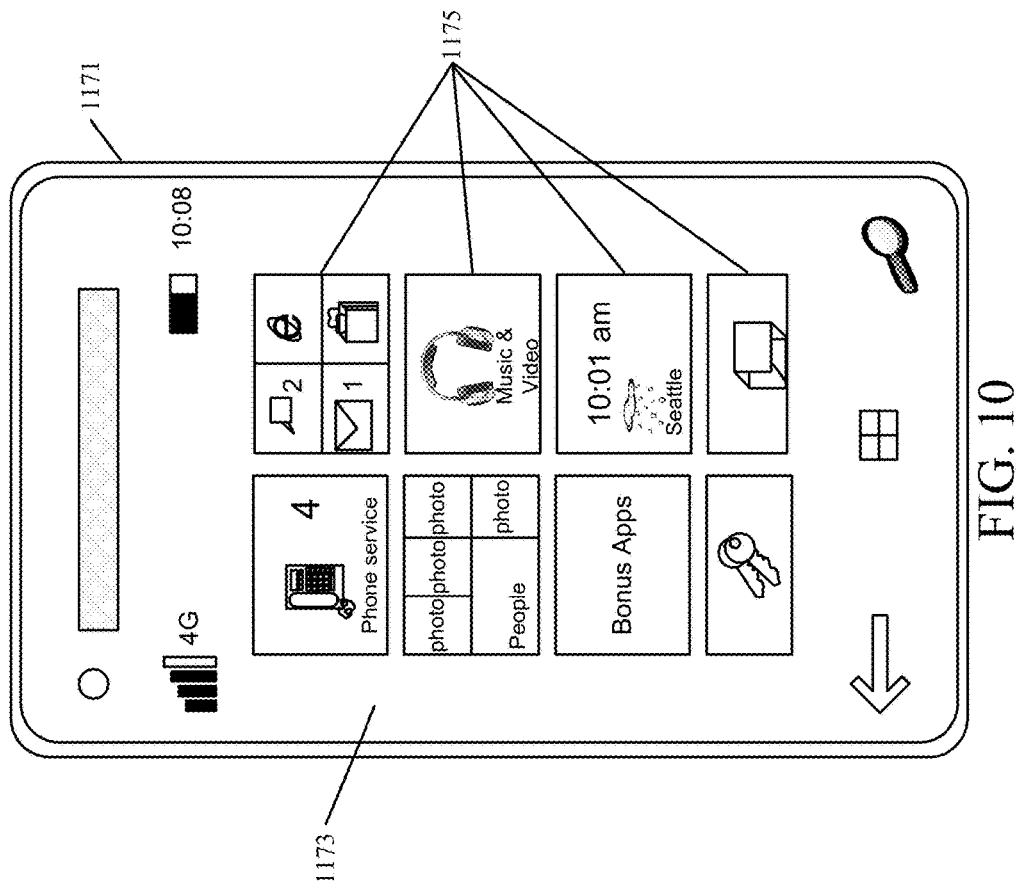

FIG. 8 is a simplified block diagram of one illustrative example of a handheld or mobile computing device that can be used as a user's or client's hand held device 916, in which the present system (or parts of it) can be deployed. For instance, a mobile device can be deployed in the operator compartment of machine 300 for use in generating, processing, or displaying the calibration zones. FIGS. 9-10 are examples of handheld or mobile devices.

FIG. 8 provides a general block diagram of the components of a client device 916 that can run some components shown in FIG. 1, that interacts with them, or both. In the device 916, a communications link 913 is provided that allows the handheld device to communicate with other computing devices and under some examples provides a channel for receiving information automatically, such as by scanning. Examples of communications link 913 include allowing communication though one or more communication protocols, such as wireless services used to provide cellular access to a network, as well as protocols that provide local wireless connections to networks.

In other examples, applications can be received on a removable Secure Digital (SD) card that is connected to an interface 915. Interface 915 and communication links 913 communicate with a processor 917 (which can also embody controller 308 from FIG. 1) along a bus 919 that is also connected to memory 921 and input/output (I/O) components 923, as well as clock 925 and location system 927.

I/O components 923, in one example, are provided to facilitate input and output operations. I/O components 923 for various examples of the device 916 can include input components such as buttons, touch sensors, optical sensors, microphones, touch screens, proximity sensors, accelerometers, orientation sensors and output components such as a display device, a speaker, and or a printer port. Other I/O components 923 can be used as well.

Clock 925 illustratively comprises a real time clock component that outputs a time and date. It can also, illustratively, provide timing functions for processor 917.

Location system 927 illustratively includes a component that outputs a current geographical location of device 916. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 921 stores operating system 929, network settings 931, applications 933, application configuration settings 935, data store 937, communication drivers 939, and communication configuration settings 941. Memory 921 can include all types of tangible volatile and non-volatile computer-readable memory devices. It can also include computer storage media (described below). Memory 921 stores computer readable instructions that, when executed by processor 17, cause the processor to perform computer-implemented steps or functions according to the instructions. Processor 917 can be activated by other components to facilitate their functionality as well.

FIG. 9 shows one example in which device 916 is a tablet computer 1000. In FIG. 9, computer 1000 is shown with user interface display screen 1002. Screen 1002 can be a touch screen or a pen-enabled interface that receives inputs from a pen or stylus. It can also use an on-screen virtual keyboard. Of course, it might also be attached to a keyboard or other user input device through a suitable attachment mechanism, such as a wireless link or USB port, for instance. Computer 1000 can also illustratively receive voice inputs as well.

FIG. 10 shows that the phone can be a smart phone 1171. Smart phone 1171 has a touch sensitive display 1173 that displays icons or tiles or other user input mechanisms 1175. Mechanisms 1175 can be used by a user to run applications, make calls, perform data transfer operations, etc. In general, smart phone 1171 is built on a mobile operating system and offers more advanced computing capability and connectivity than a feature phone.

Note that other forms of the devices 916 are possible.

Figure 11:
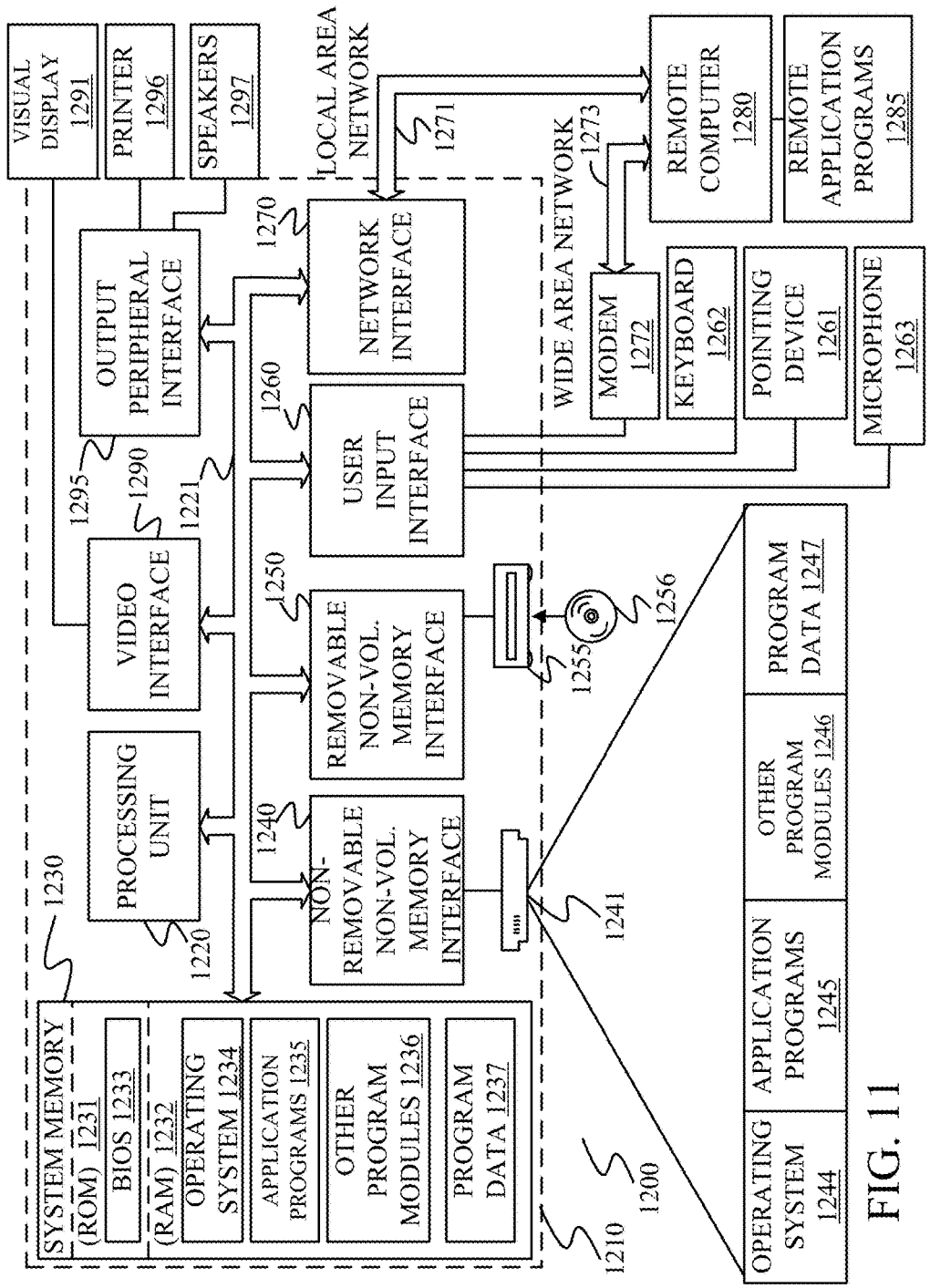
FIG. 11 is a block diagram of one example of a computing environment.

FIG. 11 is one example of a computing environment in which elements of FIG. 1, or parts of it, (for example) can be deployed. With reference to FIG. 11, an example system for implementing some examples includes a general-purpose computing device in the form of a computer 1210. Components of computer 1210, in one example, include, but are not limited to, a processing unit 1220 (which can comprise controller 308), a system memory 1230, and a system bus 1221 that couples various system components including the system memory to the processing unit 1220. The system bus 1221, in one example, is one of any of several types of bus structures including a memory bus or memory controller, a peripheral bus, and a local bus using any of a variety of bus architectures. Memory and programs described with respect to FIG. 1 can be deployed in corresponding portions of FIG. 11.

Computer 1210 typically includes a variety of computer readable media. Computer readable media can be any available media that can be accessed by computer 1210 and includes both volatile and nonvolatile media, removable and non-removable media. By way of example, and not limitation, computer readable media comprises computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 1210. Communication media, in one example, embodies computer readable instructions, data structures, program modules or other data in a transport mechanism and includes any information delivery media. The term "modulated data signal" means a signal that has one or more of its characteristics set or changed in such a manner as to encode information in the signal.

The system memory 1230 includes computer storage media in the form of volatile and/or nonvolatile memory such as read only memory (ROM) 1231 and random access memory (RAM) 1232. A basic input/output system 1233 (BIOS), containing the basic routines that help to transfer information between elements within computer 1210, such as during start-up, is typically stored in ROM 1231. RAM 1232 typically contains data and/or program modules that are immediately accessible to and/or presently being operated on by processing unit 1220. By way of example, and not limitation, FIG. 11 illustrates operating system 1234, application programs 1235, other program modules 1236, and program data 1237.

The computer 1210, in one example, also includes other removable/non-removable volatile/nonvolatile computer storage media. By way of example only, FIG. 11 illustrates a hard disk drive 1241 that reads from or writes to non-removable, nonvolatile magnetic media, a magnetic disk drive 1251, nonvolatile magnetic disk 1252, an optical disk drive 1255, and nonvolatile optical disk 1256. The hard disk drive 1241 is typically connected to the system bus 1221 through a non-removable memory interface such as interface 1240, and magnetic disk drive 1251 and optical disk drive 1255 are typically connected to the system bus 1221 by a removable memory interface, such as interface 1250.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (e.g., ASICs), Application-specific Standard Products (e.g., ASSPs), System-on-a-chip systems (SOCs), Complex Programmable Logic Devices (CPLDs), etc.

The drives and their associated computer storage media discussed above and illustrated in FIG. 11, provide storage of computer readable instructions, data structures, program modules and other data for the computer 1210. In FIG. 11, for example, hard disk drive 1241 is illustrated as storing operating system 1244, application programs 1245, other program modules 1246, and program data 1247. Note that these components can either be the same as or different from operating system 1234, application programs 1235, other program modules 1236, and program data 1237.

A user enters commands and information into the computer 1210 through input devices such as a keyboard 1262, a microphone 1263, and a pointing device 1261, such as a mouse, trackball or touch pad. Other input devices (not shown) in one example, include a joystick, game pad, satellite dish, scanner, or the like. These and other input devices are often connected to the processing unit 1220 through a user input interface 1260 that is coupled to the system bus, but in another example, is connected by other interface and bus structures. A visual display 1291 or other type of display device is also connected to the system bus 1221 via an interface, such as a video interface 1290. In addition to the monitor, computers, in one example, also include other peripheral output devices such as speakers 1297 and printer 1296, which are, in one example, connected through an output peripheral interface 1295.

The computer 1210 is operated in a networked environment using logical connections (such as a local area network—LAN, or wide area network WAN) to one or more remote computers, such as a remote computer 1280.

When used in a LAN networking environment, the computer 1210 is connected to the LAN 1271 through a network interface or adapter 1270. When used in a WAN networking environment, the computer 1210 typically includes a modem 1272 or other means for establishing communications over the WAN 1273, such as the Internet. In a networked environment, program modules, in one example, are stored in a remote memory storage device. FIG. 11 illustrates, for example, that remote application programs 1285 can reside on remote computer 1280.

It should also be noted that the different examples described herein can be combined in different ways. That is, parts of one or more examples can be combined with parts of one or more other examples. All of this is contemplated herein.

Example 1 is an agricultural sensor calibration zone computing system, comprising:

calibration zone identifier logic that receives estimated yield data indicative of estimated yield corresponding to a plurality of different areas of a field and identifies a calibration zone, in which yield sensor calibration processing is performed, in the field based on the estimated yield data; and a user interface component that surfaces an indication of the calibration zone for a user.

Example 2 is the agricultural sensor calibration zone computing system of any or all previous examples and further comprising:

a calibration system that performs the calibration processing by receiving a yield sensor signal, indicative of sensed yield sensed by a yield sensor in the calibration zone, and by determining whether a yield sensor calibration is to be performed based on the yield sensor signal.

Example 3 is the agricultural sensor calibration zone computing system of any or all previous examples wherein the calibration zone identifier logic comprises:

candidate zone identifier logic that receives the estimated yield data and identifies a candidate calibration zone, for a harvester that has a harvesting implement with an implement size, as an area in the field in which the corresponding estimated yield varies within a yield variation threshold amount and wherein the area in the field is has a size based on the implement size.

Example 4 is the agricultural sensor calibration zone computing system of any or all previous examples wherein the candidate zone identifier logic receives estimated topographic data corresponding to the field and identifies the candidate calibration zone based on the estimated topographic data.

Example 5 is the agricultural sensor calibration zone computing system of any or all previous examples wherein the candidate calibration zone identifier logic identifies the candidate calibration zone as corresponding to an area in the field in which the corresponding estimated topographic data varies within an topographic variation threshold amount.

Example 6 is the agricultural sensor calibration zone computing system of any or all previous examples wherein the calibration zone identifier logic comprises:

zone confirmation logic that receives actual yield data corresponding to the candidate calibration zone and identifies a confirmed calibration zone based on the actual yield data.

Example 7 is the agricultural sensor calibration zone computing system of any or all previous examples wherein the zone confirmation logic that receives actual topographic data corresponding to the candidate calibration zone and identifies a confirmed calibration zone based on the actual topographic data.

Example 8 is the agricultural sensor calibration zone computing system of any or all previous examples and further comprising:

an estimated yield sensor that generates the estimated yield data and provides it to the calibration zone identifier logic.

Example 9 is the agricultural sensor calibration zone computing system of any or all previous examples wherein the estimated yield sensor comprises an aerial vehicle with a yield variable sensor mounted thereon, the yield variable sensor sensing a crop characteristic indicative of estimated yield.

Example 19 is the agricultural sensor calibration zone computing system of any or all previous examples wherein the calibration zone identifier logic identifies a plurality of different calibration zones in the field in which the yield sensor can be calibrated under different harvesting conditions.

Example 11 is the agricultural sensor calibration zone computing system of any or all previous examples wherein the calibration zone identifier logic identifies the plurality of different calibration zones as corresponding to areas in the field being harvested by a harvester, wherein the areas comprise of at least one of: areas of different yields, areas of different topography, and areas of different harvester speed.

Example 12 is an agricultural machine, comprising:

a set of crop processing components that engage and process a crop in a field;

a yield sensor that senses a variable indicative of yield and generates a yield sensor signal indicative of the sensed variable;

calibration zone identifier logic that receives estimated yield data indicative of estimated yield corresponding to a plurality of different areas of the field and identifies a calibration zone in the field based on the estimated yield data, the calibration zone being an area in the field for which the yield sensor generates the corresponding yield sensor signal on which calibration processing can be performed to identify whether the yield sensor is sufficiently calibrated; and a user interface component that surfaces an indication of the calibration zone for an operator.

Example 13 is the agricultural machine of any or all previous examples wherein the calibration zone identifier logic receives topographic data indicative of a topography of the plurality of different areas of the field and identifies the calibration zone based on the topography data.

Example 14 is the agricultural machine of any or all previous examples wherein the calibration zone identifier logic identifies the calibration zone as the area in the field in which the topography data varies within a threshold topographic variation amount and wherein the estimated yield data varies within an estimated yield variation amount.

Example 15 is the agricultural machine of any or all previous examples and further comprising:

a calibration system that performs the calibration processing by receiving the yield sensor signal in the calibration zone, and by determining whether a yield sensor calibration is to be performed based on variation in the yield sensor signal.

Example 16 is the agricultural machine of any or all previous examples wherein the yield sensor comprises:

a first sectional yield sensor that generates a first yield signal indicative of yield from a first section of the crop processing components; and a second sectional yield sensor that generates a second yield signal indicative of yield from a second section of the crop processing components, wherein the calibration system determines whether the first or second sectional yield sensors are to be calibrated based on a difference between the first yield signal and the second yield signal and based on the estimated yield data for the calibration zone.

Example 17 is the agricultural machine of any or all previous examples wherein crop processing components include a harvesting implement with an implement size, and wherein the calibration zone identifier logic identifies the calibration zone as an area in the field that has a size based on the implement size.

Example 18 is a method of identifying a calibration zone for calibrating a yield sensor of a harvester, comprising:

receiving a topographical indication for a field;

calculating an area of consistent elevation in the field based at least in part on the topographical indication;

receiving an estimated yield indication for the field;

calculating an area of consistent estimated yield in the field based at least in part on the estimated yield indication;

correlating the area of consistent elevation with the area of consistent yield to identify a calibration zone comprising an area of the field with a consistent topography and a consistent estimated yield along a width and a length of the area; and surfacing the calibration zone for a user.

Example 19 is the method of any or all previous examples wherein correlating the area of consistent elevation with the area of consistent yield to identify a calibration zone comprises:

identifying the area in the field with the length based on an anticipated travel speed of the harvester through the calibration zone and a time for the harvester to reach an operational steady state within the calibration zone.

confirming, based on an in-situ analysis, that a detected elevation is within a topographical error range of the detected topographical indication.

Example 20 is the method of any or all previous examples wherein surfacing comprises:

detecting a current location of the harvester within the field;

comparing the detected current location to a location of the calibration zone; and notifying the user when the current location of the harvester is within a given distance of the location of the calibration zone.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An agricultural sensor calibration zone computing system, comprising:

calibration zone identifier logic that receives estimated yield data indicative of estimated yield corresponding to a plurality of different areas of a field and identifies a calibration zone, in which yield sensor calibration processing is performed, in the field based on the estimated yield data; and a calibration system, receiving yield data generated by a yield sensor and being indicative of a sensed yield and geographic location information indicative of a geographic location where the sensed yield was sensed, the calibration system performing the yield sensor calibration processing based on the geographic location information indicating that the geographic location where the sensed yield was sensed corresponds to the identified calibration zone.

2. The agricultural sensor calibration zone computing system of claim 1 wherein the calibration system further comprises:

a user interface component that surfaces an indication of the calibration zone for a user and a user authorization input mechanism, the calibration system, in response to receiving user actuation of the user authorization input mechanism, performing the yield sensor calibration processing.

3. The agricultural sensor calibration zone computing system of claim 1 wherein the calibration system modifies previously-received, sensed yield values, after the yield sensor calibration processing is performed.

4. The agricultural sensor calibration zone computing system of claim 1 wherein the calibration zone identifier logic comprises:

candidate zone identifier logic that receives the estimated yield data and identifies a candidate calibration zone, for a harvester that has a harvesting implement with an implement size, as an area in the field in which the corresponding estimated yield varies within a yield variation threshold amount and wherein the area in the field has a size based on the implement size.

5. The agricultural sensor calibration zone computing system of claim 4 wherein the candidate zone identifier logic receives estimated topographic data corresponding to the field and identifies the candidate calibration zone based on the estimated topographic data.

6. The agricultural sensor calibration zone computing system of claim 5 wherein the candidate calibration zone identifier logic identifies the candidate calibration zone as corresponding to an area in the field in which the corresponding estimated topographic data varies within a topographic variation threshold amount.

7. The agricultural sensor calibration zone computing system of claim 5 wherein the calibration zone identifier logic comprises:

zone confirmation logic that receives actual yield data corresponding to the candidate calibration zone and identifies a confirmed calibration zone based on the actual yield data.

8. The agricultural sensor calibration zone computing system of claim 7 wherein the zone confirmation logic that receives actual topographic data corresponding to the candidate calibration zone and identifies a confirmed calibration zone based on the actual topographic data.

9. The agricultural sensor calibration zone computing system of claim 1 and further comprising:

an estimated yield sensor that generates the estimated yield data and provides it to the calibration zone identifier logic.

10. The agricultural sensor calibration zone computing system of claim 9 wherein the estimated yield sensor comprises an aerial vehicle with a yield variable sensor mounted thereon, the yield variable sensor sensing a crop characteristic indicative of estimated yield.

11. The agricultural sensor calibration zone computing system of claim 2 wherein the calibration zone identifier logic identifies a plurality of different calibration zones in the field in which the yield sensor can be calibrated under different harvesting conditions.

12. The agricultural sensor calibration zone computing system of claim 11 wherein the calibration zone identifier logic identifies the plurality of different calibration zones as corresponding to areas in the field being harvested by a harvester, wherein the areas comprise at least one of: areas of different yields, areas of different topography, and areas of different harvester speed.

13. An agricultural machine, comprising:

a set of crop processing components that engage and process a crop in a field;

a yield sensor that senses a variable indicative of yield and generates a yield sensor signal indicative of the sensed variable;

calibration zone identifier logic that receives estimated yield data indicative of estimated yield corresponding to a plurality of different areas of the field and identifies a calibration zone in the field based on the estimated yield data, the calibration zone being an area in the field for which the yield sensor generates the corresponding yield sensor signal on which calibration processing can be performed to identify whether the yield sensor is sufficiently calibrated; and a calibration system that performs calibration processing by receiving the yield sensor signal in the calibration zone, and by determining whether a yield sensor calibration is to be performed based on variation in the yield sensor signal.

14. The agricultural machine of claim 13 wherein the calibration zone identifier logic receives topographic data indicative of a topography of the plurality of different areas of the field and identifies the calibration zone based on the topography data.

15. The agricultural machine of claim 14 wherein the calibration zone identifier logic identifies the calibration zone as the area in the field in which the topography data varies within a threshold topographic variation amount and wherein the estimated yield data varies within an estimated yield variation amount.

16. The agricultural machine of claim 15 wherein the yield sensor comprises:

a first sectional yield sensor that generates a first yield signal indicative of yield from a first section of the crop processing components; and a second sectional yield sensor that generates a second yield signal indicative of yield from a second section of the crop processing components, wherein the calibration system determines whether the first or second sectional yield sensors are to be calibrated based on a difference between the first yield signal and the second yield signal and based on the estimated yield data for the calibration zone.

17. The agricultural machine of claim 15 wherein crop processing components include a harvesting implement with an implement size, and wherein the calibration zone identifier logic identifies the calibration zone as an area in the field that has a size based on the implement size.

18. A method of identifying a calibration zone for calibrating a yield sensor of a harvester, comprising:

receiving a topographical indication for a field;

calculating an area of consistent elevation in the field based at least in part on the topographical indication;

receiving an estimated yield indication for the field;

calculating an area of consistent estimated yield in the field based at least in part on the estimated yield indication;

correlating the area of consistent elevation with the area of consistent yield to identify a calibration zone comprising an area of the field with a consistent topography and a consistent estimated yield along a width and a length of the area; and calibrating the yield sensor based on a yield signal generated by the yield sensor in the calibration zone.

19. The method of claim 18 wherein correlating the area of consistent elevation with the area of consistent yield to identify a calibration zone comprises:

identifying the area in the field with the length based on an anticipated travel speed of the harvester through the calibration zone and a time for the harvester to reach an operational steady state within the calibration zone; and confirming, based on an in-situ analysis, that a detected elevation is within a topographical error range of the detected topographical indication.

20. The method of claim 19 wherein calibrating the yield sensor comprises at least one of:

adjusting yield values generated based on the yield signal during current operation in the field;

adjusting yield values that were generated based on the yield signal prior to current operation in the field; or waiting to adjust yield values until operation in the field is complete, and, thereafter, adjusting the yield values that were generated during operation in the field.

* * * * *